(12) United States Patent
Nadzadi et al.

(10) Patent No.: US 12,151,377 B2
(45) Date of Patent: Nov. 26, 2024

(54) SYSTEMS AND METHODS FOR PROVIDING HAPTIC GUIDANCE

(71) Applicant: MAKO Surgical Corp., Fort Lauderdale, FL (US)

(72) Inventors: Mark Nadzadi, Memphis, TN (US); Rishabh Khurana, Fort Lauderdale, FL (US)

(73) Assignee: MAKO Surgical Corp., Weston, FL (US)

( * ) Notice: Subject to any disclaimer, the term of this patent is extended or adjusted under 35 U.S.C. 154(b) by 98 days.

(21) Appl. No.: 17/257,192

(22) PCT Filed: Sep. 24, 2020

(86) PCT No.: PCT/US2020/052466
§ 371 (c)(1),
(2) Date: Dec. 30, 2020

(87) PCT Pub. No.: WO2021/067113
PCT Pub. Date: Apr. 8, 2021

(65) Prior Publication Data
US 2022/0305653 A1  Sep. 29, 2022

Related U.S. Application Data

(60) Provisional application No. 62/908,890, filed on Oct. 1, 2019.

(51) Int. Cl.
*B25J 9/16* (2006.01)
*A61B 34/00* (2016.01)
(Continued)

(52) U.S. Cl.
CPC ............. *B25J 9/1664* (2013.01); *A61B 34/37* (2016.02); *A61B 34/76* (2016.02); *A61B 34/77* (2016.02); *B25J 13/06* (2013.01)

(58) Field of Classification Search
CPC ......... B25J 9/1664; B25J 13/06; A61B 34/37; A61B 34/76; A61B 34/77; A61B 34/25;
(Continued)

(56) References Cited

U.S. PATENT DOCUMENTS 8,010,180 B2  8/2011  Quaid et al.
8,498,744 B2  7/2013  Odermatt et al.
(Continued)

FOREIGN PATENT DOCUMENTS

JP  H08-117238 A  5/1996
JP  2007-534351 A  11/2007

OTHER PUBLICATIONS

International Search Report and Written Opinion for International Application No. PCT/US2020/052466, mailed Jan. 27, 2021, 10 pages.
(Continued)

*Primary Examiner* — Adam R Mott
*Assistant Examiner* — Matthew C Gammon
(74) *Attorney, Agent, or Firm* — FOLEY & LARDNER LLP

(57) ABSTRACT

A method includes defining a virtual object and defining a first point and a second point associated with a virtual representation of a surgical tool. Movement of the virtual representation of the surgical tool corresponds to movement of the surgical tool in real space. The method includes controlling a robotic device coupled to the surgical tool to constrain the first point to the virtual object, determining that the first point is at a threshold position along the virtual object, and controlling the robotic device to guide the second point to the virtual object.

19 Claims, 13 Drawing Sheets

(51) Int. Cl.
*A61B 34/37* (2016.01)
*B25J 13/06* (2006.01)

(58) Field of Classification Search
CPC .............. A61B 34/32; A61B 2034/105; A61B 2034/107; A61B 2034/2055; A61B 2090/065; A61B 34/20; A61B 34/10; A61B 34/30; A61B 17/1764
See application file for complete search history.

(56) References Cited

U.S. PATENT DOCUMENTS

| | | |
|---|---|---|
| 9,289,264 B2 | 3/2016 | Iorgulescu et al. |
| 9,588,583 B2 | 3/2017 | Lightcap et al. |
| 9,636,185 B2 | 5/2017 | Quaid et al. |
| 9,655,683 B2 | 5/2017 | Iorgulescu et al. |
| 10,004,565 B2 | 6/2018 | Kang et al. |
| 10,575,913 B2 | 3/2020 | Iorgulescu et al. |
| 10,610,301 B2 | 4/2020 | Quaid, III |
| 2008/0088620 A1 | 4/2008 | Shih et al. |
| 2009/0000627 A1 | 1/2009 | Quaid et al. |
| 2009/0012531 A1 | 1/2009 | Quaid et al. |
| 2013/0172902 A1 | 7/2013 | Lightcap et al. |
| 2013/0172905 A1* | 7/2013 | Iorgulescu ............ A61B 34/20 606/130 |
| 2014/0031664 A1 | 1/2014 | Kang et al. |
| 2014/0180290 A1 | 6/2014 | Otto et al. |
| 2015/0320500 A1 | 11/2015 | Lightcap et al. |
| 2015/0324114 A1 | 11/2015 | Hurley et al. |
| 2016/0199136 A1 | 7/2016 | Iorgulescu et al. |
| 2017/0020613 A1 | 1/2017 | Kang et al. |
| 2017/0151021 A1* | 6/2017 | Quaid, III ............ A61B 34/70 |
| 2018/0014894 A1* | 1/2018 | Hagag ................ A61B 17/1631 |
| 2018/0116739 A1* | 5/2018 | Gogarty ................ A61B 34/10 |
| 2018/0303568 A1 | 10/2018 | Iorgulescu et al. |
| 2018/0325608 A1 | 11/2018 | Kang et al. |
| 2019/0083191 A1 | 3/2019 | Gilhooley et al. |
| 2019/0133791 A1 | 5/2019 | Yadav et al. |
| 2022/0160440 A1* | 5/2022 | Jaramaz ................ A61B 90/50 |

OTHER PUBLICATIONS

Safavi et al., Model-based Haptic Guidance in Surgical Skill Improvement, IEEE International Conference on Systems, Man, and Cybernetics, Oct. 2015, 6 pages.

Invitation to Pay Additional Fees for International Application No. PCT/US2020/052466, mailed Nov. 5, 2020, 2 pages.

* cited by examiner

SYSTEMS AND METHODS FOR PROVIDING HAPTIC GUIDANCE

CROSS-REFERENCE TO RELATED APPLICATIONS

This application claims the benefit of and priority to U.S. Provisional Patent Application No. 62/908,890, filed Oct. 1, 2019, the entire disclosure of which is incorporated by reference herein.

BACKGROUND

The present disclosure relates generally to surgical systems for orthopedic surgeries, for example surgical systems that facilitate joint replacement procedures. Joint replacement procedures (arthroplasty procedures) are widely used to treat osteoarthritis and other damage to a patient's joint by replacing portions of the joint with prosthetic components. Joint replacement procedures can include procedures to replace hips, knees, shoulders, or other joints with one or more prosthetic components.

One possible tool for use in an arthroplasty procedure is a robotically-assisted surgical system. A robotically-assisted surgical system typically includes a robotic device that is used to prepare a patient's anatomy to receive an implant, a tracking system configured to monitor the location of the robotic device relative to the patient's anatomy, and a computing system configured to monitor and control the robotic device. Robotically-assisted surgical systems, in various forms, autonomously carry out surgical tasks, provide force feedback to a user manipulating a surgical device to complete surgical tasks, augment surgeon dexterity and precision, and/or provide other navigational cues to facilitate safe and accurate surgical operations.

A surgical plan is typically established prior to performing a surgical procedure with a robotically-assisted surgical system. Based on the surgical plan, the surgical system guides, controls, or limits movements of the surgical tool during portions of the surgical procedure. Guidance and/or control of the surgical tool serves to assist the surgeon during implementation of the surgical plan.

SUMMARY

Figure 1:
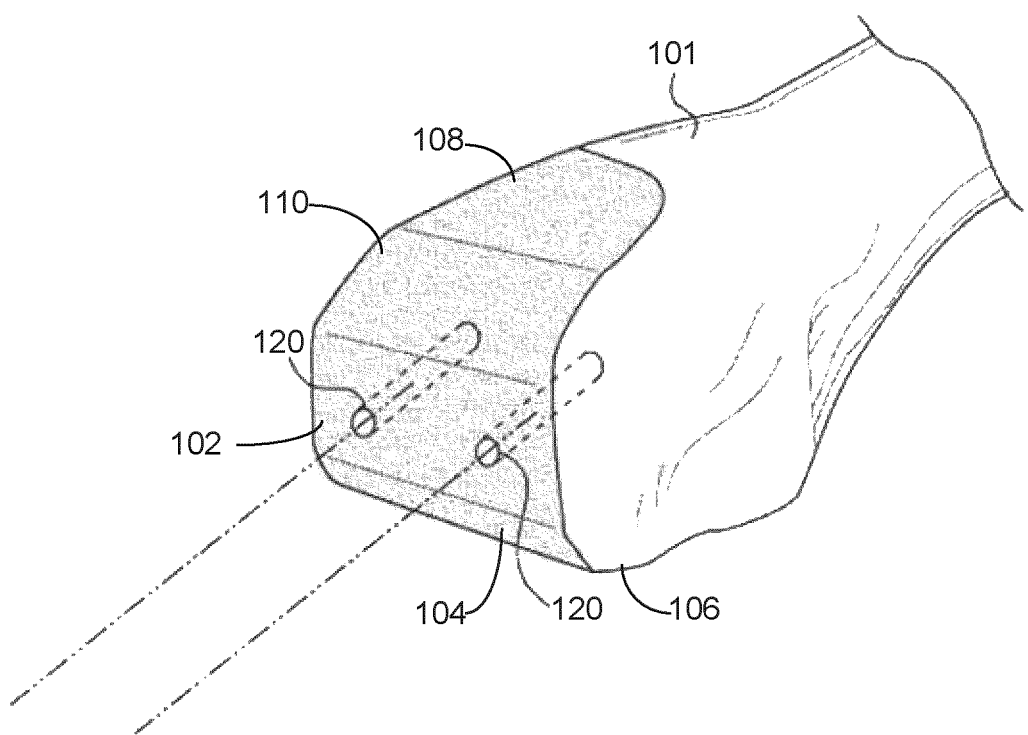
FIG. 1 is a perspective view of a femur prepared to receive an implant component, according to an exemplary embodiment.

One implementation of the present disclosure is a method for controlling a robotic device. The method includes defining a virtual object and defining a first point and a second point associated with a virtual representation of a surgical tool. Movement of the virtual representation of the surgical tool corresponds to movement of the surgical tool in real space. The method includes controlling the robotic device coupled to the surgical tool to constrain the first point to the virtual object, determining that the first point is at a threshold position along the virtual object, and controlling the robotic device to guide the second point to the virtual object.

Another implementation of the present disclosure is a system including a robotic device and a processing circuit communicable with the robotic device. The processing circuit can be configured to define a virtual object and define a first point and a second point associated with a virtual representation of a surgical tool. The processing circuit is configured so that movement of the virtual representation of the surgical tool corresponds to movement of the surgical tool in real space. The processing circuit is further configured to control the robotic device coupled to the surgical tool to constrain the first point to the virtual object, determine that the first point is at a threshold position along the virtual object, and control the robotic device to guide the second point to the virtual object.

Another implementation of the present disclosure is a method of operating a robotic device having a tool coupled thereto. The method includes controlling the robotic device to constrain the surgical tool based on a first haptic object, receiving a signal and a user defined direction, and adjusting a haptic control interaction in response to the signal by extending the first haptic object in the user-defined direction.

Another implementation of the present disclosure is a system including a robotic device and a processing circuit communicable with the robotic device. The processing circuit is configured to control the robotic device to constrain the surgical tool based on a first haptic object, receive a signal and a user defined direction, and adjust a haptic control interaction in response to the signal by extending the first haptic object in the user-defined direction.

Another implementation of the present disclosure is a method of operating a robotic device having a tool coupled thereto. The method includes controlling the robotic device to constrain the tool based on a first haptic object, receiving a signal and a user defined direction, and adjusting a haptic control interaction in response to the signal by adjusting a virtual dimension of the tool.

Another implementation of the present disclosure is a system including a robotic device and a processing circuit communicable with the robotic device. The processing circuit is configured to control the robotic device to constrain the tool based on a first haptic object, receive a signal and a user defined direction, and adjust a haptic control interaction in response to the signal by adjusting a virtual dimension of the tool.

Another implementation of the present disclosure is a method of operating a robotic device. The method includes tracking movement of a tool coupled to the robotic device, determining a direction of movement of the tool, determining whether the direction of movement points towards a virtual control object, and, in response to a determination that the direction of movement points towards the virtual control object, controlling the robotic device to guide the tool to the virtual control object.

Another implementation of the present disclosure is a system including a robotic device and a processing circuit communicable with the robotic device. The processing circuit is configured to receive tracking data indicative of movement of a tool coupled to the robotic device, determine a direction of movement of the tool, determine whether the direction of movement points towards a virtual control object, and, in response to a determination that the direction of movement points towards the virtual control object, control the robotic device to guide the tool to the virtual control object.

Another implementation of the present disclosure is a method of operating a robotic device. The method includes tracking a tool coupled to a robotic device, controlling the robotic device to constrain the tool within a virtual control object, defining a zone of the virtual control object, determining that the tool is in the zone, and controlling the robotic device to resist movement of the tool in the zone.

Another implementation of the present disclosure is a system including a robotic device and a processing circuit communicable with the robotic device. The processing circuit is configured to control the robotic device to constrain the tool within a virtual control object, define a zone of the virtual control object, determine that the tool is in the zone, and control the robotic device to resist movement of the tool in the zone.

Another implementation of the present disclosure is a method of operating a robotic device having a tool coupled thereto. The method includes constraining, by the robotic device, the tool to a virtual control object, detecting a force exerted on the tool in approximately a pre-determined direction, determining whether the force in approximately the pre-determined direction exceeds a threshold force, and in response to a determination that the force in approximately the pre-determined direction exceeds a threshold force, controlling the robotic device to allow the tool to exit the virtual control object.

Another implementation of the present disclosure is a system including a robotic device and a processing circuit communicable with the robotic device. The processing circuit is configured to control the robotic device to constrain the tool to a virtual control object, detect a force exerted on the tool in approximately a pre-determined direction, determine whether the force in approximately the pre-determined direction exceeds a threshold force, and in response to a determination that the force in approximately the pre-determined direction exceeds a threshold force, control the robotic device to allow the tool to exit the virtual control object.

DETAILED DESCRIPTION

Presently preferred embodiments of the invention are illustrated in the drawings. An effort has been made to use the same or like reference numbers throughout the drawings to refer to the same or like parts. Although this specification refers primarily to a robotic arm for orthopedic joint replacement, it should be understood that the subject matter described herein is applicable to other types of robotic systems, including those used for non-surgical applications, as well as for procedures directed to other anatomical regions, for example spinal or dental procedures.

Referring now to FIG. 1, a femur 101 as modified during a knee arthroplasty procedure is shown, according to an exemplary embodiment. As shown in FIG. 1, the femur 101 has been modified with multiple planar cuts. In the example shown, the femur 100 has been modified by five substantially planar cuts to create five substantially planar surfaces, namely distal surface 102, posterior chamfer surface 104, posterior surface 106, anterior surface 108, and anterior chamfer surface 110. The planar surfaces may be achieved using a sagittal saw or other surgical tool, for example a surgical tool coupled to a robotic device as in the examples described below. The planar surfaces 102-110 are created such that the planar surfaces 102-110 will mate with corresponding surfaces of a femoral implant component. The positions and angular orientations of the planar surfaces 102-110 may determine the alignment and positioning of the implant component. Accordingly, operating a surgical tool to create the planar surfaces 102-110 with a high degree of accuracy may improve the outcome of a joint replacement procedure.

As shown in FIG. 1, the femur 101 has also been modified to have a pair of pilot holes 120. The pilot holes 120 extend into the femur 101 and are created such that the pilot holes 120 can receive a screw, a projection extending from a surface of an implant component, or other structure configured to facilitate coupling of an implant component to the femur 101. The pilot holes 120 may be created using a drill, spherical burr, or other surgical tool as described below. The pilot holes 120 may have a pre-planned position, orientation, and depth, which facilitates secure coupling of the implant component to the bone in a desired position and orientation. In some cases, the pilot holes 120 are planned to intersect with higher-density areas of a bone and/or to avoid other implant components and/or sensitive anatomical features. Accordingly, operating a surgical tool to create the pilot holes 120 with a high degree of accuracy may improve the outcome of a joint replacement procedure.

In some embodiments, the systems and methods described herein provide robotic assistance for creating the planar surfaces 102-110 and the pilot holes 120. It should be understood that the creation of five planar cuts and two cylindrical pilot holes as shown in FIG. 1 is an example only, and that the systems and methods described herein may be adapted to plan and facilitate creation of any number of planar or non-planar cuts, any number of pilot holes, any combination thereof, etc., for preparation of any bone and/or joint in various embodiments. For example, in a hip or shoulder arthroplasty procedure, a spherical burr may be used in accordance with the systems and methods herein to ream a curved surface configured to receive a curved implant cup. Furthermore, in other embodiments, the systems and methods described herein may be used to facilitate placement an implant component relative to a bone (e.g., to facilitate impaction of cup implant in a hip arthroplasty procedure). Many such surgical and non-surgical implementations are within the scope of the present disclosure.

Figure 2:
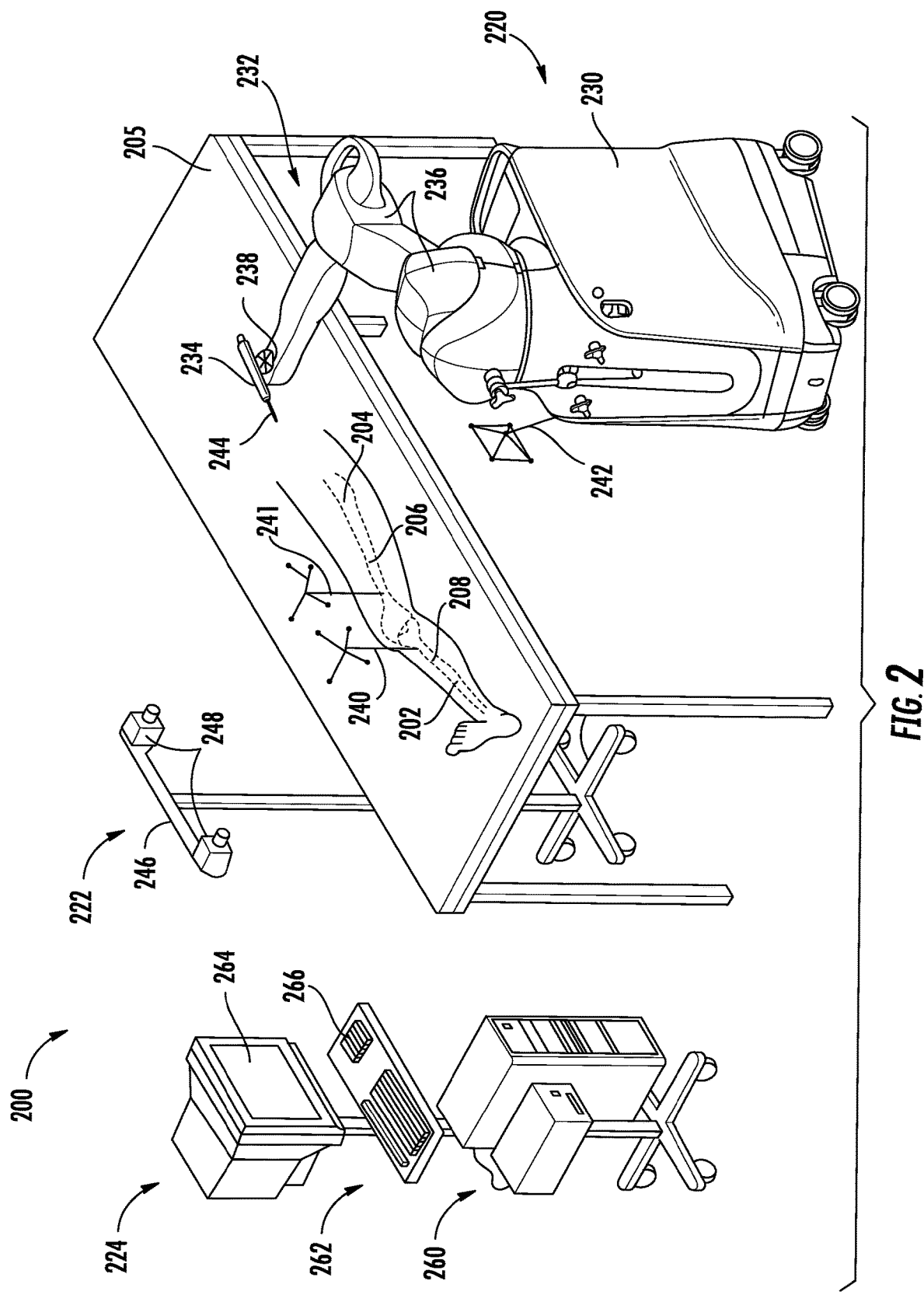
FIG. 2 is an illustration of a surgical system, according to an exemplary embodiment.

Referring now to FIG. 2, a surgical system 200 for orthopedic surgery is shown, according to an exemplary embodiment. In general, the surgical system 200 is configured to facilitate the planning and execution of a surgical plan, for example to facilitate a joint-related procedure. As shown in FIG. 2, the surgical system 200 is set up to treat a leg 202 of a patient 204 sitting or lying on table 205. In the illustration shown in FIG. 2, the leg 202 includes femur 206 (e.g., femur 101 of FIG. 1) and tibia 208, between which a prosthetic knee implant is to be implanted in a total knee arthroscopy procedure. In other scenarios, the surgical system 200 is set up to treat a hip of a patient, i.e., the femur and the pelvis of the patient. Additionally, in still other scenarios, the surgical system 200 is set up to treat a shoulder of a patient, i.e., to facilitate replacement and/or augmentation of components of a shoulder joint (e.g., to facilitate placement of a humeral component, a glenoid component, and a graft or implant augment). Various other anatomical regions and procedures are also possible. To facilitate the procedure, surgical system 200 includes robotic device 220, tracking system 222, and computing system 224.

The robotic device 220 is configured to modify a patient's anatomy (e.g., femur 206 of patient 204) under the control of the computing system 224. One embodiment of the robotic device 220 is a haptic device. "Haptic" refers to a sense of touch, and the field of haptics relates to, among other things, human interactive devices that provide feedback to an operator. Feedback may include tactile sensations such as, for example, vibration. Feedback may also include providing force to a user, such as a positive force or a resistance to movement. One use of haptics is to provide a user of the device with guidance or limits for manipulation of that device. For example, a haptic device may be coupled to a surgical tool, which can be manipulated by a surgeon to perform a surgical procedure. The surgeon's manipulation of the surgical tool can be guided or limited through the use of haptics to provide feedback to the surgeon during manipulation of the surgical tool.

Another embodiment of the robotic device 220 is an autonomous or semi-autonomous robot. "Autonomous" refers to a robotic device's ability to act independently or semi-independently of human control by gathering information about its situation, determining a course of action, and automatically carrying out that course of action. For example, in such an embodiment, the robotic device 220, in communication with the tracking system 222 and the computing system 224, may autonomously complete the series of femoral cuts mentioned above without direct human intervention.

The robotic device 220 includes a base 230, a robotic arm 232, and a surgical tool 234, and is communicably coupled to the computing system 224 and the tracking system 222. The base 230 provides a moveable foundation for the robotic arm 232, allowing the robotic arm 232 and the surgical tool 234 to be repositioned as needed relative to the patient 204 and the table 205. The base 230 may also contain power systems, computing elements, motors, and other electronic or mechanical system necessary for the functions of the robotic arm 232 and the surgical tool 234 described below.

The robotic arm 232 is configured to support the surgical tool 234 and provide a force as instructed by the computing system 224. In some embodiments, the robotic arm 232 allows a user to manipulate the surgical tool and provides force feedback to the user. In such an embodiment, the robotic arm 232 includes joints 236 and mount 238 that include motors, actuators, or other mechanisms configured to allow a user to freely translate and rotate the robotic arm 232 and surgical tool 234 through allowable poses while providing force feedback to constrain or prevent some movements of the robotic arm 232 and surgical tool 234 as instructed by computing system 224. As described in detail below, the robotic arm 232 thereby allows a surgeon to have full control over the surgical tool 234 within a control object while providing force feedback along a boundary of that object (e.g., a vibration, a force preventing or resisting penetration of the boundary). In some embodiments, the robotic arm is configured to move the surgical tool to a new pose automatically without direct user manipulation, as instructed by computing system 224, in order to position the robotic arm as needed and/or complete certain surgical tasks, including, for example, cuts in a femur 206.

The surgical tool 234 is configured to cut, burr, grind, drill, partially resect, reshape, and/or otherwise modify a bone, or to constrain/limit movement of a device used to cut, burr, grind, drill, partially resect, reshape, and/or otherwise modify a bone. The surgical tool 234 may be any suitable tool, and may be one of multiple tools interchangeably connectable to robotic device 220. For example, as shown in FIG. 2 the surgical tool 234 includes a spherical burr 244. In other examples, the surgical tool may also be a sagittal saw, for example with a blade aligned parallel with a tool axis or perpendicular to the tool axis. The surgical tool may also be a drill, for example with a rotary bit aligned parallel with a tool axis or perpendicular to the tool axis. The surgical tool 234 may be a jig, drill guide, cutting guide, etc. in various embodiments, for example configured to have a saw, drill, or other instrument inserted therethrough. The surgical tool 234 may also be a holding arm or other support configured to hold an implant component (e.g., cup 28a, implant augment, etc.) in position while the implant component is screwed to a bone, adhered (e.g., cemented) to a bone or other implant component, or otherwise installed in a preferred position. In some embodiments, the surgical tool 234 is an impaction tool configured to provide an impaction force to a cup implant to facilitate fixation of the cup implant to a pelvis in a planned location and orientation.

Tracking system 222 is configured track the patient's anatomy (e.g., femur 206 and tibia 208) and the robotic device 220 (i.e., surgical tool 234 and/or robotic arm 232) to enable control of the surgical tool 234 coupled to the robotic arm 232, to determine a position and orientation of modifications or other results made by the surgical tool 234, and allow a user to visualize the bones (e.g., femur 206, the tibia 208, pelvis, humerus, scapula, etc. as applicable in various procedures), the surgical tool 234, and/or the robotic arm 232 on a display of the computing system 224. More particularly, the tracking system 222 determines a position and orientation (i.e., pose) of objects (e.g., surgical tool 234, femur 206) with respect to a coordinate frame of reference and tracks (i.e., continuously determines) the pose of the objects during a surgical procedure. According to various embodiments, the tracking system 222 may be any type of navigation system, including a non-mechanical tracking system (e.g., an optical tracking system), a mechanical tracking system (e.g., tracking based on measuring the relative angles of joints 236 of the robotic arm 232), or any combination of non-mechanical and mechanical tracking systems.

In the embodiment shown in FIG. 2, the tracking system 222 includes an optical tracking system. Accordingly, tracking system 222 includes a first fiducial tree 240 coupled to the tibia 208, a second fiducial tree 241 coupled to the femur 206, a third fiducial tree 242 coupled to the base 230, one or more fiducials coupled to surgical tool 234, and a detection device 246 configured to detect the three-dimensional position of fiducials (i.e., markers on fiducial trees 240-242).

Fiducial trees 240, 241 may be coupled to other bones as suitable for various procedures (e.g., pelvis and femur in a hip arthroplasty procedure). Detection device 246 may be an optical detector such as a camera or infrared sensor. The fiducial trees 240-242 include fiducials, which are markers configured to show up clearly to the optical detector and/or be easily detectable by an image processing system using data from the optical detector, for example by being highly reflective of infrared radiation (e.g., emitted by an element of tracking system 222). A stereoscopic arrangement of cameras on detection device 246 allows the position of each fiducial to be determined in 3D-space through a triangulation approach. Each fiducial has a geometric relationship to a corresponding object, such that tracking of the fiducials allows for the tracking of the object (e.g., tracking the second fiducial tree 241 allows the tracking system 222 to track the femur 206), and the tracking system 222 may be configured to carry out a registration process to determine or verify this geometric relationship. Unique arrangements of the fiducials in the fiducial trees 240-242 (i.e., the fiducials in the first fiducial tree 240 are arranged in a different geometry than fiducials in the second fiducial tree 241) allows for distinguishing the fiducial trees, and therefore the objects being tracked, from one another.

Using the tracking system 222 of FIG. 2 or some other approach to surgical navigation and tracking, the surgical system 200 can determine the position of the surgical tool 234 relative to a patient's anatomical feature, for example femur 206, as the surgical tool 234 is used to modify the anatomical feature or otherwise facilitate the surgical procedure. Additionally, using the tracking system 222 of FIG. 2 or some other approach to surgical navigation and tracking, the surgical system 200 can determine the relative poses of the tracked bones.

The computing system 224 is configured to create a surgical plan, control the robotic device 220 in accordance with the surgical plan to make one or more bone modifications and/or facilitate implantation of one or more prosthetic components. Accordingly, the computing system 224 is communicably coupled to the tracking system 222 and the robotic device 220 to facilitate electronic communication between the robotic device 220, the tracking system 222, and the computing system 224. Further, the computing system 224 may be connected to a network to receive information related to a patient's medical history or other patient profile information, medical imaging, surgical plans, surgical procedures, and to perform various functions related to performance of surgical procedures, for example by accessing an electronic health records system. Computing system 224 includes processing circuit 260 and input/output device 262.

The input/output device 262 is configured to receive user input and display output as needed for the functions and processes described herein. As shown in FIG. 2, input/output device 262 includes a display 264 and a keyboard 266. The display 264 is configured to display graphical user interfaces generated by the processing circuit 260 that include, for example, information about surgical plans, medical imaging, settings and other options for surgical system 200, status information relating to the tracking system 222 and the robotic device 220, and tracking visualizations based on data supplied by tracking system 222. The keyboard 266 is configured to receive user input to those graphical user interfaces to control one or more functions of the surgical system 200.

The processing circuit 260 includes a processor and memory device. The processor can be implemented as a general purpose processor, an application specific integrated circuit (ASIC), one or more field programmable gate arrays (FPGAs), a group of processing components, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit 260 and includes computer code for executing (e.g., by the processing circuit 260 and/or processor) one or more processes described herein.

More particularly, processing circuit 260 is configured to facilitate the creation of a preoperative surgical plan prior to the surgical procedure. According to some embodiments, the preoperative surgical plan is developed utilizing a three-dimensional representation of a patient's anatomy, also referred to herein as a "virtual bone model." A "virtual bone model" may include virtual representations of cartilage or other tissue in addition to bone. To obtain the virtual bone model, the processing circuit 260 receives imaging data of the patient's anatomy on which the surgical procedure is to be performed. The imaging data may be created using any suitable medical imaging technique to image the relevant anatomical feature, including computed tomography (CT), magnetic resonance imaging (MRI), and/or ultrasound. The imaging data is then segmented (i.e., the regions in the imaging corresponding to different anatomical features are distinguished) to obtain the virtual bone model. For example, MM-based scan data of a joint can be segmented to distinguish bone from surrounding ligaments, cartilage, previously-implanted prosthetic components, and other tissue to obtain a three-dimensional model of the imaged bone.

Alternatively, the virtual bone model may be obtained by selecting a three-dimensional model from a database or library of bone models. In one embodiment, the user may use input/output device 262 to select an appropriate model. In another embodiment, the processing circuit 260 may execute stored instructions to select an appropriate model based on images or other information provided about the patient. The selected bone model(s) from the database can then be deformed based on specific patient characteristics, creating a virtual bone model for use in surgical planning and implementation as described herein.

A preoperative surgical plan can then be created based on the virtual bone model. The surgical plan may be automatically generated by the processing circuit 260, input by a user via input/output device 262, or some combination of the two (e.g., the processing circuit 260 limits some features of user-created plans, generates a plan that a user can modify, etc.). In some embodiments, the surgical plan may be generated and/or modified based on distraction force measurements collected intraoperatively.

The preoperative surgical plan includes the desired cuts, holes, surfaces, burrs, or other modifications to a patient's anatomy to be made using the surgical system 200. For example, for a total knee arthroscopy procedure, the preoperative plan may include the cuts necessary to form, on a femur, a distal surface, a posterior chamfer surface, a posterior surface, an anterior surface, and an anterior chamfer surface in relative orientations and positions suitable to be mated to corresponding surfaces of the prosthetic to be joined to the femur during the surgical procedure, as well as cuts necessary to form, on the tibia, surface(s) suitable to mate to the prosthetic to be joined to the tibia during the surgical procedure. As another example, the preoperative plan may include the modifications necessary to create holes (e.g., pilot holes 120) in a bone. As another example, in a hip arthroplasty procedure, the surgical plan may include the burr necessary to form one or more surfaces on the acetabular region of the pelvis to receive a cup and, in suitable cases, an implant augment. Accordingly, the processing circuit 260 may receive, access, and/or store a model of the prosthetic to facilitate the generation of surgical plans.

The processing circuit 260 is further configured to generate a control object for the robotic device 220 in accordance with the surgical plan. The control object may take various forms according to the various types of possible robotic devices (e.g., haptic, autonomous). For example, in some embodiments, the control object defines instructions for the robotic device to control the robotic device to move within the control object (i.e., to autonomously make one or more cuts of the surgical plan guided by feedback from the tracking system 222). In some embodiments, the control object includes a visualization of the surgical plan and the robotic device on the display 264 to facilitate surgical navigation and help guide a surgeon to follow the surgical plan (e.g., without active control or force feedback of the robotic device). In embodiments where the robotic device 220 is a haptic device, the control object may be a haptic object as described in the following paragraphs.

In an embodiment where the robotic device 220 is a haptic device, the processing circuit 260 is further configured to generate one or more haptic objects based on the preoperative surgical plan to assist the surgeon during implementation of the surgical plan by enabling constraint of the surgical tool 234 during the surgical procedure. A haptic object may be formed in one, two, or three dimensions. For example, a haptic object can be a line, a plane, or a three-dimensional volume. A haptic object may be curved with curved surfaces and/or have flat surfaces, and can be any shape, for example a funnel shape. Haptic objects can be created to represent a variety of desired outcomes for movement of the surgical tool 234 during the surgical procedure. One or more of the boundaries of a three-dimensional haptic object may represent one or more modifications, such as cuts, to be created on the surface of a bone. A planar haptic object may represent a modification, such as a cut, to be created on the surface of a bone. A curved haptic object may represent a resulting surface of a bone as modified to receive a cup implant and/or implant augment. A line haptic object may correspond to a pilot hole to be made in a bone to prepare the bone to receive a screw or other projection.

In an embodiment where the robotic device 220 is a haptic device, the processing circuit 260 is further configured to generate a virtual tool representation of the surgical tool 234. The virtual tool includes one or more haptic interaction points (HIPs), which represent and are associated with locations on the physical surgical tool 234. In an embodiment in which the surgical tool 234 is a spherical burr (e.g., as shown in FIG. 2), a HIP may represent the center of the spherical burr. Where one HIP is used to virtually represent a surgical tool, the HIP may be referred to herein as a tool center point (TCP). If the surgical tool 234 is an irregular shape, for example as for a sagittal saw, the virtual representation of the sagittal saw may include numerous HIPs. Using multiple HIPs to generate haptic forces (e.g. positive force feedback or resistance to movement) on a surgical tool is described in U.S. application Ser. No. 13/339,369, titled "System and Method for Providing Substantially Stable Haptics," filed Dec. 28, 2011, and hereby incorporated by reference herein in its entirety. In one embodiment of the present invention, a virtual tool representing a sagittal saw includes eleven HIPs. As used herein, references to an "HIP" are deemed to also include references to "one or more HIPs." As described below, relationships between HIPs and haptic objects enable the surgical system 200 to constrain the surgical tool 234.

Prior to performance of the surgical procedure, the patient's anatomy (e.g., femur 206) is registered to the virtual bone model of the patient's anatomy by any known registration technique. One possible registration technique is point-based registration, as described in U.S. Pat. No. 8,010, 180, titled "Haptic Guidance System and Method," granted Aug. 30, 2011, and hereby incorporated by reference herein in its entirety. Alternatively, registration may be accomplished by 2D/3D registration utilizing a hand-held radiographic imaging device, as described in U.S. application Ser. No. 13/562,163, titled "Radiographic Imaging Device," filed Jul. 30, 2012, and hereby incorporated by reference herein in its entirety. Registration also includes registration of the surgical tool 234 to a virtual tool representation of the surgical tool 234, so that the surgical system 200 can determine and monitor the pose of the surgical tool 234 relative to the patient (i.e., to femur 206). Registration of allows for accurate navigation, control, and/or force feedback during the surgical procedure. Additional details relating to registration for hip arthroplasty procedures in some embodiments are described in detail below.

The processing circuit 260 is configured to monitor the virtual positions of the virtual tool representation, the virtual bone model, and the control object (e.g., virtual haptic objects) corresponding to the real-world positions of the patient's bone (e.g., femur 206), the surgical tool 234, and one or more lines, planes, or three-dimensional spaces defined by forces created by robotic device 220. For example, if the patient's anatomy moves during the surgical procedure as tracked by the tracking system 222, the processing circuit 260 correspondingly moves the virtual bone model. The virtual bone model therefore corresponds to, or is associated with, the patient's actual (i.e. physical) anatomy and the position and orientation of that anatomy in real/physical space. Similarly, any haptic objects, control objects, or other planned automated robotic device motions created during surgical planning that are linked to cuts, modifications, etc. to be made to that anatomy also move in correspondence with the patient's anatomy. In some embodiments, the surgical system 200 includes a clamp or brace to substantially immobilize the femur 206 to minimize the need to track and process motion of the femur 206.

For embodiments where the robotic device 220 is a haptic device, the surgical system 200 is configured to constrain the surgical tool 234 based on relationships between HIPs and haptic objects. That is, when the processing circuit 260 uses data supplied by tracking system 222 to detect that a user is manipulating the surgical tool 234 to bring a HIP in virtual contact with a haptic object, the processing circuit 260 generates a control signal to the robotic arm 232 to provide haptic feedback (e.g., a force, a vibration) to the user to communicate a constraint on the movement of the surgical tool 234. In general, the term "constrain," as used herein, is used to describe a tendency to restrict movement. However, the form of constraint imposed on surgical tool 234 depends on the form of the relevant haptic object. A haptic object may be formed in any desirable shape or configuration. As noted above, three exemplary embodiments include a line, plane, or three-dimensional volume. In one embodiment, the surgical tool 234 is constrained because a HIP of surgical tool 234 is restricted to movement along a linear haptic object. In another embodiment, the haptic object is a three-dimensional volume and the surgical tool 234 may be constrained by substantially preventing movement of the HIP outside of the volume enclosed by the walls of the three-dimensional haptic object. In another embodiment, the surgical tool 234 is constrained because a planar haptic object substantially prevents movement of the HIP outside of the plane and outside of the boundaries of the planar haptic object. For example, the processing circuit 260 can establish a planar haptic object corresponding to a planned planar distal cut needed to create a distal surface on the femur 206 in order to confine the surgical tool 234 substantially to the plane needed to carry out the planned distal cut.

For embodiments where the robotic device 220 is an autonomous device, the surgical system 200 is configured to autonomously move and operate the surgical tool 234 in accordance with the control object. For example, the control object may define areas relative to the femur 206 for which a cut should be made. In such a case, one or more motors, actuators, and/or other mechanisms of the robotic arm 232 and the surgical tool 234 are controllable to cause the surgical tool 234 to move and operate as necessary within the control object to make a planned cut, for example using tracking data from the tracking system 222 to allow for closed-loop control.

Figure 3:
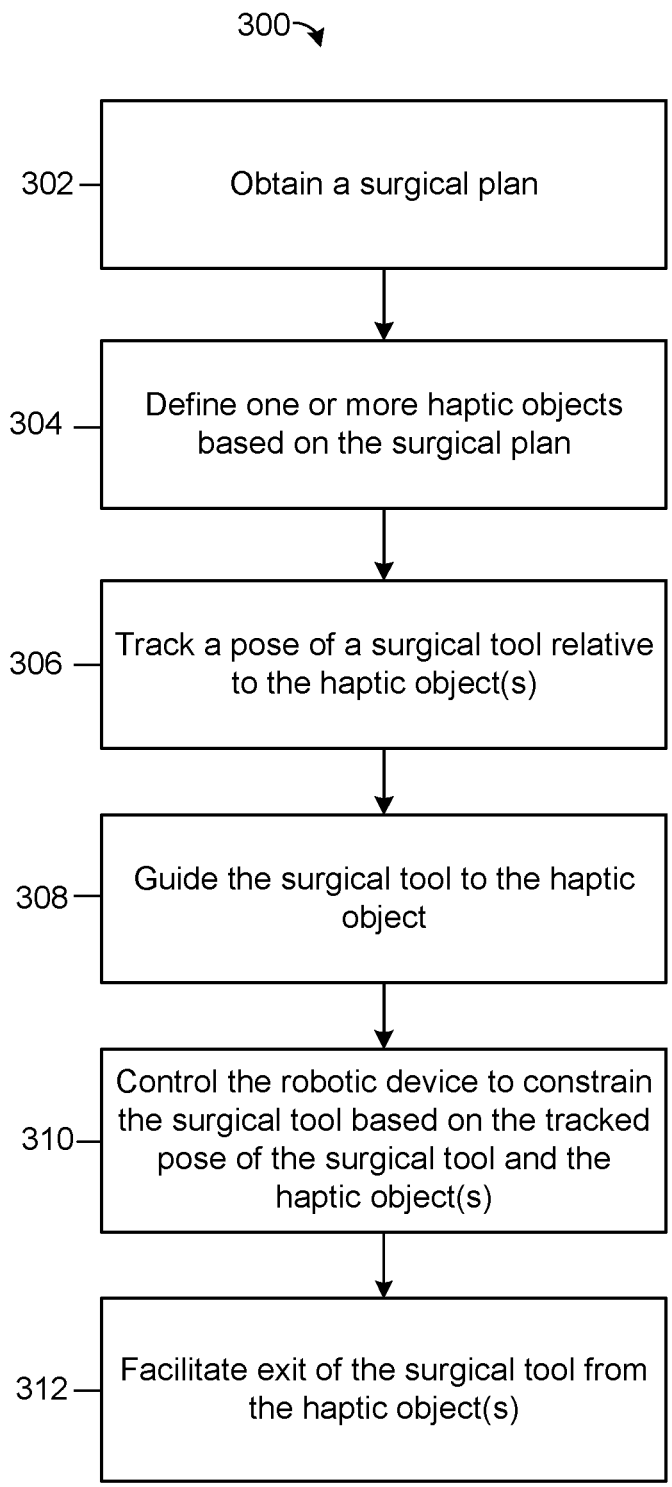
FIG. 3 is a flowchart of a first process that can be executed by the surgical system of FIG. 2, according to an exemplary embodiment.

Referring now to FIG. 3, a flowchart of a process 300 that can be executed by the surgical system 200 of FIG. 2 is shown, according to an exemplary embodiment. Process 300 may be adapted to facilitate various surgical procedures, including total and partial joint replacement surgeries. Process 300 may be executed using various steps and features shown in FIGS. 4-13 and described in detail below, including combinations thereof.

At step 302, a surgical plan is obtained. The surgical plan (e.g., a computer-readable data file) may define a desired outcome of bone modifications, for example defined based on a desired position of prosthetic components relative to the patient's anatomy. For example, in the case of a knee arthroplasty procedure, the surgical plan may provide pre-planned positions and orientations of the planar surfaces 102-110 and the pilot holes 120 as shown in FIG. 1. The surgical plan may be generated based on medical imaging, 3D modeling, surgeon input, etc.

At step 304, one or more control boundaries, such as haptic objects, are defined based on the surgical plan. The one or more haptic objects may be one-dimensional (e.g., a line haptic), two dimensional (i.e., planar), or three dimensional (e.g., cylindrical, funnel-shaped, curved, etc.). The haptic objects may represent planned bone modifications (e.g., a haptic object for each of the planar surfaces 102-110 and each of the pilot holes 120 shown in FIG. 1), implant components, surgical approach trajectories, etc. defined by the surgical plan. The haptic objects can be oriented and positioned in three-dimensional space relative to a tracked position of a patient's anatomy.

At step 306, a pose of a surgical tool is tracked relative to the haptic object(s), for example by the tracking system 222 described above. In some embodiments, one point on the surgical tool is tracked. In other embodiments, (e.g., in the example of FIGS. 4-5) two points on the surgical tool are tracked, for example a tool center point (TCP) at a tip/ effective end of the surgical tool and a second interaction point (SIP) positioned along a body or handle portion of the surgical tool. In other embodiments, three or more points on the surgical tool are tracked. A pose of the surgical tool is ascertained relative to a coordinate system in which the one or more haptic objects are defined and, in some embodiments, in which the pose of one or more anatomical features of the patient is also tracked.

At step 308, the surgical tool is guided to the haptic object(s). For example, the display 264 of the surgical system 200 may display a graphical user interface instructing a user on how (e.g., which direction) to move the surgical tool and/or robotic device to bring the surgical tool to a haptic object. As another example, the surgical tool may be guided to a haptic object using a collapsing haptic boundary as described in U.S. Pat. No. 9,289,264, the entire disclosure of which is incorporated by reference herein. As another example, the robotic device may be controlled to automatically move the surgical tool to a haptic object. As another example, step 308 may be executed using the process 800 of FIG. 8 which is described in detail below.

Figure 4:
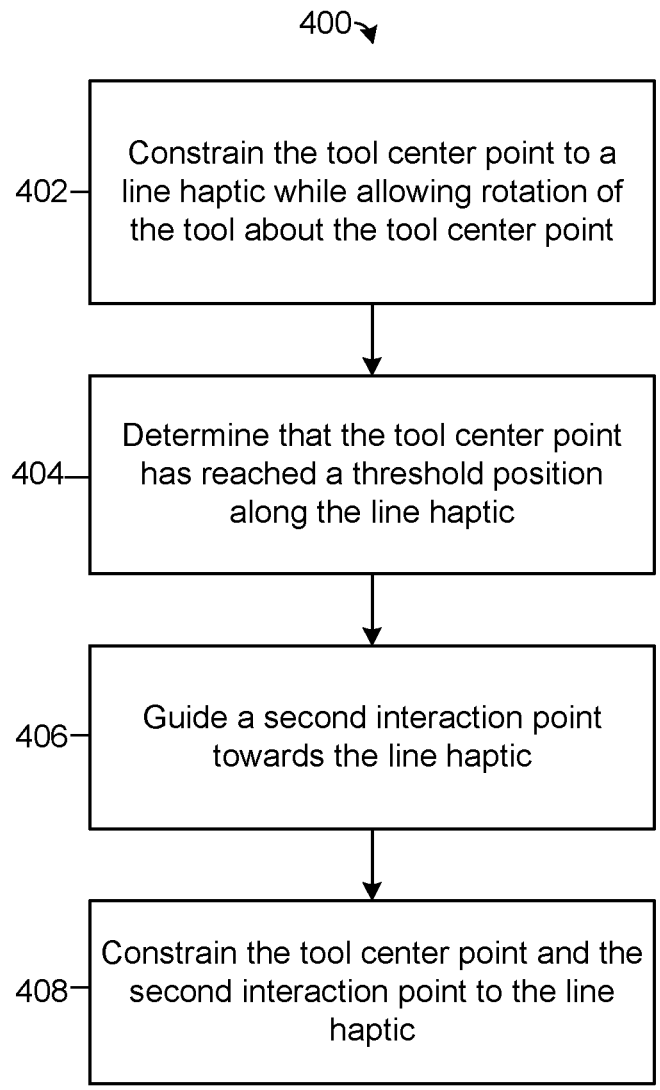
FIG. 4 is a flowchart of a second process that can be executed by the surgical system of FIG. 2, according to an exemplary embodiment.
Figure 5:
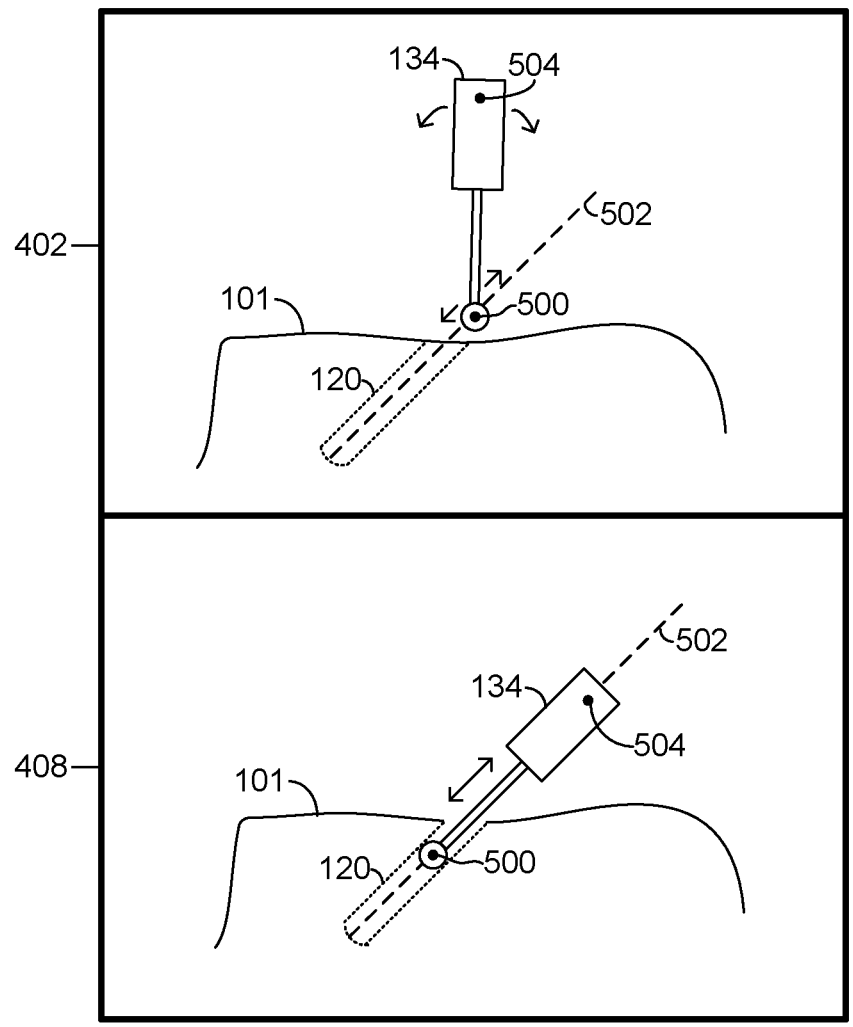
FIG. 5 is an illustration of the process of FIG. 4, according to an exemplary embodiment.
Figure 9:
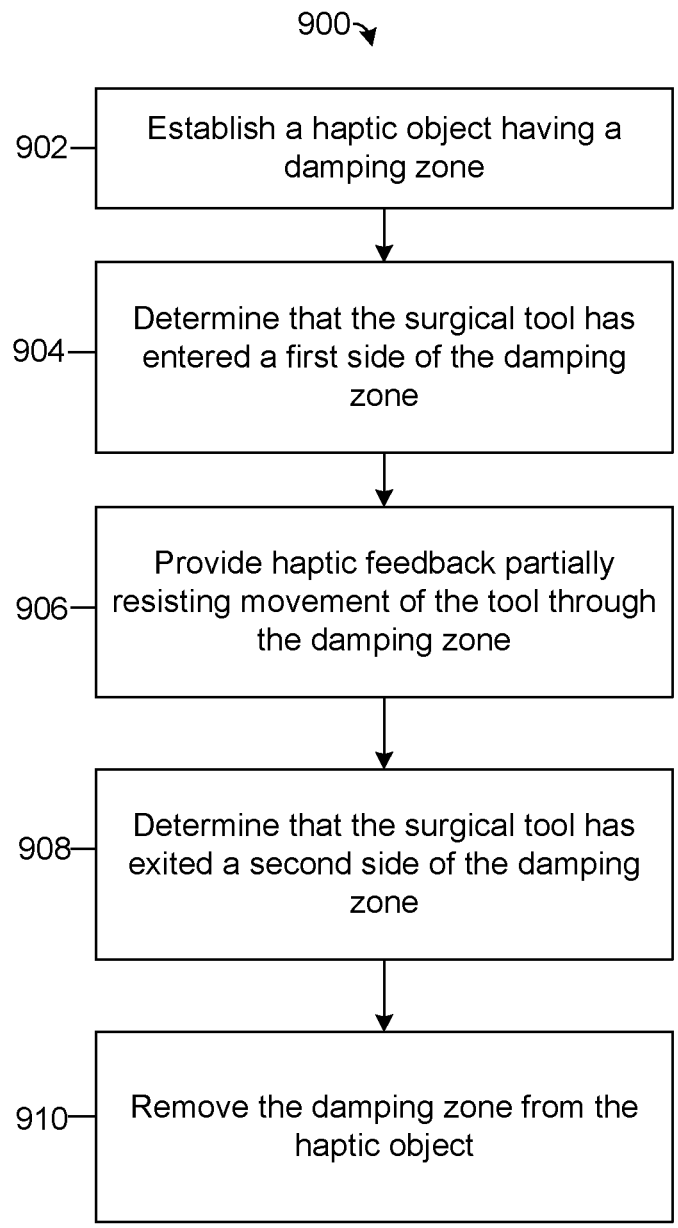
FIG. 9 is a flowchart of a fifth process that can be executed by the surgical system of FIG. 2, according to an exemplary embodiment.
Figure 10:
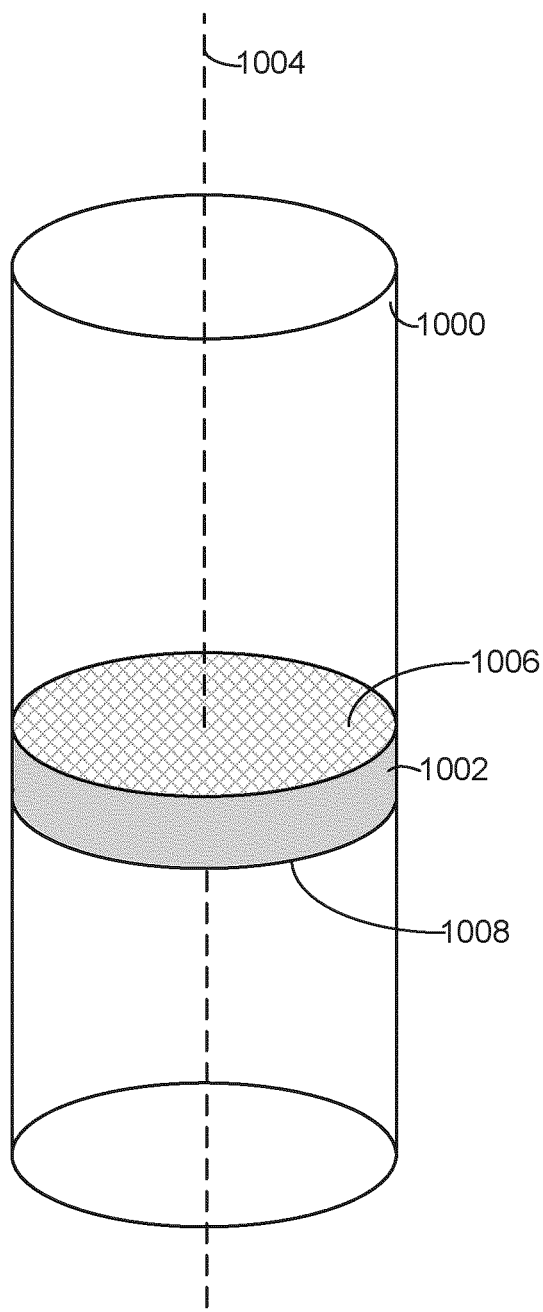
FIG. 10 is an illustration of a virtual control object that can be used with the process of FIG. 9, according to an exemplary embodiment.

At step 310, the robotic device is controlled to constrain movement of the surgical tool based on the tracked pose of the surgical tool and the poses of one or more haptic objects. The constraining of the surgical tool may be achieved as described above with reference to FIG. 2. In some embodiments, step 310 includes a two-phase approach as shown in FIGS. 4-5 and described with reference thereto below. In some embodiments, step 310 includes providing a damping force that resists movement of the surgical tool through a particular zone, for example as shown in FIGS. 9-10 and described with reference thereto below. In some embodiments, step 310 includes adjusting a haptic interaction in response to a user input, for example according to the examples of FIGS. 11-13 described with reference thereto below. Various combinations of these features are possible at step 310.

Figure 6:
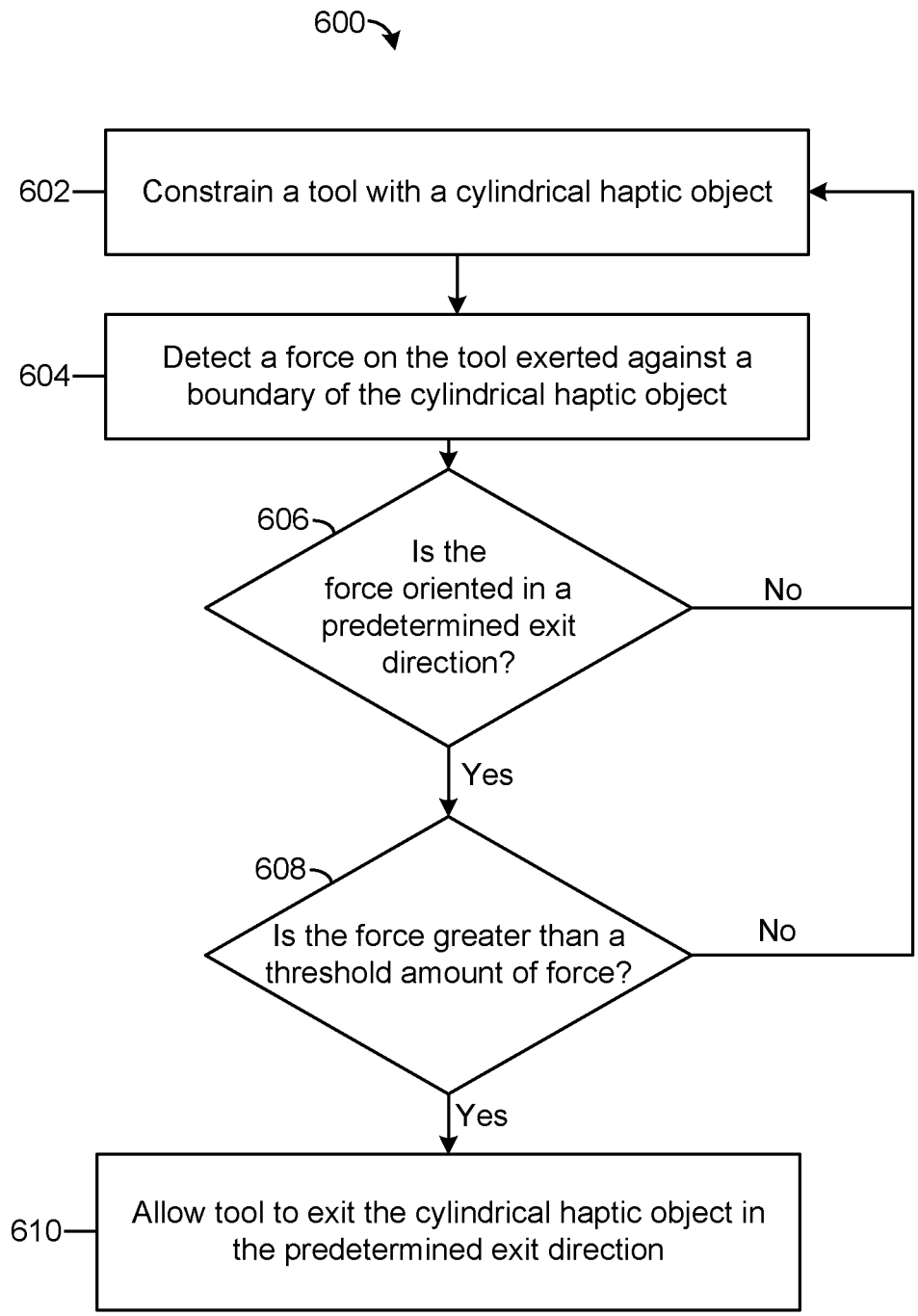
FIG. 6 is a flowchart of a third process that can be executed by the surgical system of FIG. 2, according to an exemplary embodiment.
Figure 7:
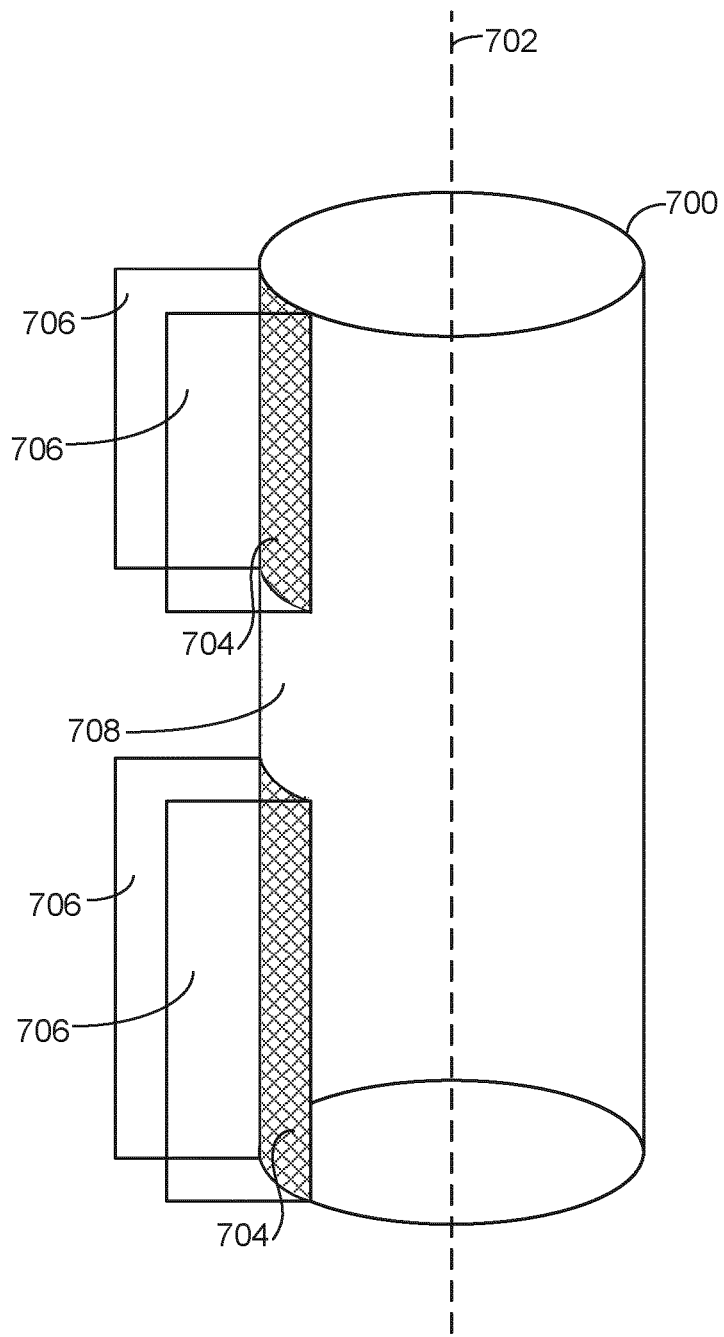
FIG. 7 is an illustration of a virtual control object that can be used with the process of FIG. 6, according to an exemplary embodiment.

At step 312, exit of the surgical tool from the haptic object(s) is facilitated, i.e., to release the constraints of a haptic object. For example, in some embodiments, the robotic device is controlled to allow the surgical tool to exit a haptic object along an axis of the haptic object. In some embodiments, for example as shown in FIGS. 6-7 and described in detail with reference thereto below, the surgical tool may be allowed to exit the haptic object in a pre-determined direction relative to the haptic object. The surgical tool may thereby be removed from the surgical field and the haptic object to facilitate subsequent steps of the surgical procedure. Additionally, it should be understood that, in some cases, the process 300 may return to step 308 where the surgical tool is guided to the same or different haptic object after exiting a haptic object at step 312.

Process 300 may thereby be executed by the surgical system 200 to facilitate a surgical procedure. Features of process 300 are shown in FIGS. 4-13 below according to some embodiments, and such features can be combined in various combinations in various embodiments and/or based on settings selected for a particular procedure. Furthermore, it should be understood that the features of FIGS. 4-13 may be provided while omitting some or all other steps of process 300. All such possibilities are within the scope of the present disclosure.

Referring now to FIGS. 4-5, a two-phase haptic interaction is depicted, according to an exemplary embodiment. FIG. 4 shows a flowchart of a process 400 for providing a two-phase haptic interaction, while FIG. 5 shows a storyboard-style illustration of the two-phase haptic interaction (i.e., of process 400). Process 400 can be executed by the surgical system 200, for example at step 310 of process 300.

At step 402, the tool center point (TCP) 500 is constrained to a line haptic 502 while allowing rotation of the surgical tool 234 about the tool center point 500 and translation of the TCP 500 along the line haptic 502. The line haptic 502 may correspond to a planned bone modification, for example a planned pilot hole 120 as shown in FIG. 1. The line haptic 502 may be defined as the axis of the planned pilot hole 120 and may extend from a bottom (deepest end) of the planned pilot hole 120, extending beyond the anatomical feature (e.g., femur 101). The line haptic 502 is a straight line in example of FIG. 5. In other embodiments, the line haptic 502 may be curved, for example defined as a spline. In other embodiments, the process 400 of FIG. 4 may be adapted to use a planar haptic object, volumetric haptic object, or a haptic object defined as any combination of lines, planes, and/or volumes in place of the line haptic 502.

The TCP 500 is tracked relative to the line haptic 502, and the robotic device is controlled to constrain the TCP 500 to remain on or substantially on the line haptic 502 (e.g., prevent or resist deviation from the line haptic 502, provide a springing force driving the TCP 500 back to the line haptic 502, etc.). The TCP 500 can be translated along the line haptic 502 at step 402. The robotic device is controlled (e.g., via admittance control) to allow surgical tool 234 to be rotated (e.g., as manipulated by a user) about the TCP 500. That is, a second interaction point (SIP) 504 located along a handle or body portion of the surgical tool 234 is unconstrained at step 402.

Rotation of the surgical tool 234 about the TCP 500 at step 402 may facilitate a surgeon in reaching the line haptic 502 along a preferred approach trajectory. In some cases, surrounding soft tissue and/or bone structures may make it difficult or impossible for the surgical tool 234 to be inserted from a position fully outside of the patient to the bone surface along the line haptic 502 without causing undesirable or unnecessary disruption to the surrounding tissue or bone (e.g., without requiring a hole to be created though such tissue or bone). In such a case, the surgical tool 234 can be inserted along a preferred trajectory until the TCP 500 reaches the line haptic 502 and is constrained by the line haptic 502. At step 402, the surgical tool 234 can be rotated to displace anatomical features by pushing such features with a side of the shaft or body of the surgical tool. By constraining the TCP 500 to the line haptic 502, a surgeon is allowed to focus on rotating the surgical tool 234 as desired at step 402 without the burden of also monitoring the position of the TCP 500 and/or attempting to manually prevent movement of the TCP 500 away from the desired axis. Step 402 may thereby facilitate insertion and orientation of the surgical tool 234 in various anatomical regions.

At step 404, a determination is made (e.g., by the processing circuit 260) that the TCP 500 has reached a threshold position along the line haptic 502. In some cases, the threshold position is a defined based on distance away from a surface of a bone (e.g., femur 101), such that the threshold position is reached before the surgical tool 234 contacts the bone. In such cases, steps 406-408 may be executed as described below before the surgical tool 234 begins to modify the bone, thereby ensuring the desired orientation of the surgical tool 234 before initiation of bone modification.

In other cases, the threshold position is defined based on a depth below the surface of the bone, such that the threshold position is reached after the surgical tool 234 contacts the bone. In such cases, the surgical tool 234 may be allowed to begin modifying the bone at a first orientation before being rotated into alignment with the line haptic 502 as described below with reference to steps 406-408, for example to reduce a risk of skiving or otherwise facilitate entry of the surgical tool 234 into the bone. As shown in FIG. 5, for example, initial contact may be made between the surgical tool 234 and the bone 101 with the surgical tool approximately normal to the surface of the bone as shown in the upper frame (i.e., during step 402), which may improve the likelihood of achieving a clean initial cut/bore/drill/etc. into the bone 101 at the planned location (i.e., at the intersection between the line haptic 502 and the bone 101). In such a case, the determination that the TCP 500 has reached the threshold position may then be made after initial penetration of the surgical tool 234 into the bone 101 (i.e., such that the TCP 500 has crossed a surface of the bone 101).

At step 406, in response to a determination that the TCP 500 has reached the threshold position at step 404, the SIP 504 is guided towards the line haptic 502. In some embodiments, the robotic device may be controlled to provide an assistive force that assists a user is rotating the surgical tool 234 about the TCP 500 to move the SIP 504 towards the line haptic 502. In some embodiments, a collapsing haptic object is used at step 406 which prevents rotation of the SIP 504 away from the line haptic 502 while allowing rotation of the SIP 504 towards the line haptic 502. In some embodiments, guiding the SIP 504 towards the line haptic 502 is achieved by displaying instructions via display 264. In some embodiments, guiding the SIP 504 towards the line haptic 502 is achieved by controlling the robotic device to automatically rotate the surgical tool 234 to align the SIP 504 with the line haptic 502. The TCP 500 is constrained to the line haptic 502 (as described for step 402) during step 406 (i.e., while the SIP 504 is guided to the line haptic 502). In some cases, the robotic device is controlled to prevent translation of the TCP 500 along the line haptic 502 while the SIP 504 is guided to the line haptic 502 during step 406.

At step 408, after the SIP 504 has been guided to the line haptic 502 as a result of step 406, the robotic device is controlled to constrain the TCP 500 and the SIP 504 to the line haptic 502. The surgical tool 234 can be translated along the line haptic 502 to execute the planned bone modification (e.g., to create a pilot hole 120). In the example shown, the SIP 504 is located along an axis of the surgical tool 234. Thus, by constraining two points of other surgical tool 234 to the line haptic 502 (i.e., the TCP 500 and the SIP 504), alignment of the surgical tool 234 with the line haptic 502 is maintained. In other embodiments, the SIP 504 is guided to a second haptic (i.e., a different virtual haptic object than the line haptic 502). In such an embodiment, the TCP 500 and the SIP 504 are the confined to different haptic objects. For example, in a case where the surgical tool 234 is curved, the SIP 504 may be confined to a curved line while the TCP 500 is confined to a straight line (or vice versa) in order to achieve a desired freedom and restriction of movement of the surgical tool 234.

Other geometries and behaviors may also be enabled by using different haptic objects for the SIP 504 and the TCP 500. For example, the TCP 500 may be confined to a haptic objection corresponding to the geometry of a planned cut or drill path, while the SIP 504 is confined to a different haptic object which is configured to prevent or resist collisions between the shaft of the surgical tool 234 (or other point on the robotic arm) with one or more objects in the surgical field. For example, the SIP 504 may be confined to a haptic object having a geometry based on the positions of retractors or other tools in the surgical field (e.g., tracked retractor positions). As another example, the SIP 504 may be confined to a haptic object having a geometry based on positions of anatomical features, for example corresponding to a shape of a surgical port or other incision or opening through which the shaft of the surgical tool 234 extends during execution of a planned bone preparation. Control of the robotic device can thereby be configured to confine the TCP 502 to a first haptic object and the SIP 504 to a second haptic object to guide the TCP 502 in accordance with a planned bone preparation while avoiding unwanted behaviors of a tool shaft by confining the SIP 504. Process 400 can thus be executed by the surgical system 200 to provide accurate bone modification in a reliable and intuitive manner.

Referring now to FIGS. 6-7, a process 600 for facilitating exit of a surgical tool from a haptic object is illustrated, according to an exemplary embodiment. FIG. 6 shows a flowchart of the process 600, while FIG. 7 depicts a haptic object that may be used with the process 600 of FIG. 6. Process 600 can be executed by the surgical system 200, for example at step 312 of process 300. Although the example of FIGS. 6-7 contemplates a cylindrical haptic object, it should be understood that process 600 may be adapted to control objects having various geometries.

At step 602, the robotic device is controlled to constrain the surgical tool 234 with a cylindrical haptic object. FIG. 7 shows an example of a cylindrical haptic object 700 centered on a target axis 702. In some embodiments, the cylindrical haptic object 700 corresponds to a surgical approach trajectory and/or a planned bone modification (e.g., a planned pilot hole 120). The cylindrical haptic object 700 may extend substantially beyond (away from) a sensitive anatomical region. With the surgical tool 234 constrained in the cylindrical haptic object 700, the surgical tool 234 may partially obstruct access to the surgical field. Accordingly, it may be desirable for a surgeon to move the surgical tool out of the cylindrical haptic object 700 in a safe direction to facilitate various steps of a surgical procedure.

At step 604, a force on the surgical tool 234 exerted against a boundary of the cylindrical haptic object is detected. The force can be detected by the robotic device 220, for example as a wrench exerted on joints of a robotic arm 232. For example, a HIP associated with the surgical tool 234 may be positioned at a boundary of the cylindrical haptic object 700 while a user exerts a force on the surgical tool 234 pushing the surgical tool 234 against or into the boundary.

At step 606, a determination is made (e.g., by the processing circuit 260) of whether the force detected at step 604 is oriented in a predetermined exit direction. The predetermined exit direction may be chosen as a safe and/or convenient direction in which the surgical tool 234 can be allowed to exit the haptic object. For example, in the predetermined exit direction is defined by an exit region 704 of the cylindrical haptic object 700 and walls 706 that extend from the cylindrical haptic object 700 at the exit region 704. In such an example, the processing circuit 260 can determine that the force is oriented in the predetermined exit direction if a HIP of the surgical tool 234 is at the exit region 704 as the force is against the boundary of the cylindrical haptic object 700. In some embodiments, the exit region 704 only spans a portion of a length of the haptic object 700, for example interrupted with a dead zone 708 as shown in FIG. 7. As another example, in some embodiments the processing circuit 260 can determine a direction vector that points the direction in which the user is forcing the tool. In such a case, a determination can be made of whether the direction vector is within a threshold angle of the predetermined exit direction. In this example, if the direction vector is within the threshold angle of the predetermined exit direction, the force is considered to be directed in the predetermined exit direction (i.e., "Yes" at step 606). The resulting exit boundary may thereby take on the shape of a funnel.

If the force is not oriented in the predetermined exit direction, the process 600 returns to step 602 and the surgical tool 234 is constrained with the cylindrical haptic object 700. That is, the robotic device 220 is controlled to provide force feedback to constrain the surgical tool from exiting the cylindrical haptic object 700, for example to facilitate one or more steps of a surgical procedure.

If the force is oriented in the predetermined exit direction (as determined at step 606), a determination is made (e.g., by the processing circuit 260) at step 608 regarding whether the force is greater than a threshold amount of force. In some embodiments, the amount of force exerted on the surgical tool 234 may be measured by joints of the robotic arm 232. A user may indicate a desire to exit the haptic object by exceeding the threshold amount of force, while the threshold amount of force can be set high enough to substantially prevent an accidental or unintentional exit from the haptic object.

If the force is less than the threshold amount of force, the robotic device 220 is controlled to constrain the surgical tool 234 from exiting the haptic object (e.g., from passing through the exit region 704 of the cylindrical haptic object 700). The process 600 returns to step 602 and the surgical tool 234 continues to be constrained with the cylindrical haptic object 700 to facilitate use of the surgical tool 234 in executing of a step of a surgical procedure.

If a determination is made that the force exceeds the threshold amount of force at step 608, at step 610 the surgical tool is allowed to exit the haptic object in the predetermined exit direction. In the example of FIG. 7, a constraint associated with the exit region 704 is removed such that the surgical tool 234 is allowed to move through the exit region 704 to exit the cylindrical haptic object 700. The walls 706 may be included as haptic boundaries to guide the surgical tool 234 away from the axis 702 in the predetermined direction. In other words, the surgical tool 234 can be pushed across the exit region 704 of the cylindrical haptic object 700 to exit the cylindrical haptic object in the predetermined direction.

The surgical tool 234 is therefore allowed to exit a haptic object, such that the robotic device is no longer controlled to constrain the surgical tool 234 with the haptic object. In some cases, the surgical tool 234 can be reinserted into the haptic object (i.e., to restart haptic constraint) via the exit region 704 and/or using any other haptic initiation procedure (e.g., following the process of FIG. 8). In some cases, the haptic object is removed (deleted, etc.) when the surgical tool 234 exits the haptic object. In some cases, the haptic object is adjusted or a new haptic object is activated to facilitate a subsequent step of the surgical procedure. Process 600 may thereby be executed one or more times by the surgical procedure to facilitate a surgical procedure.

Figure 8:
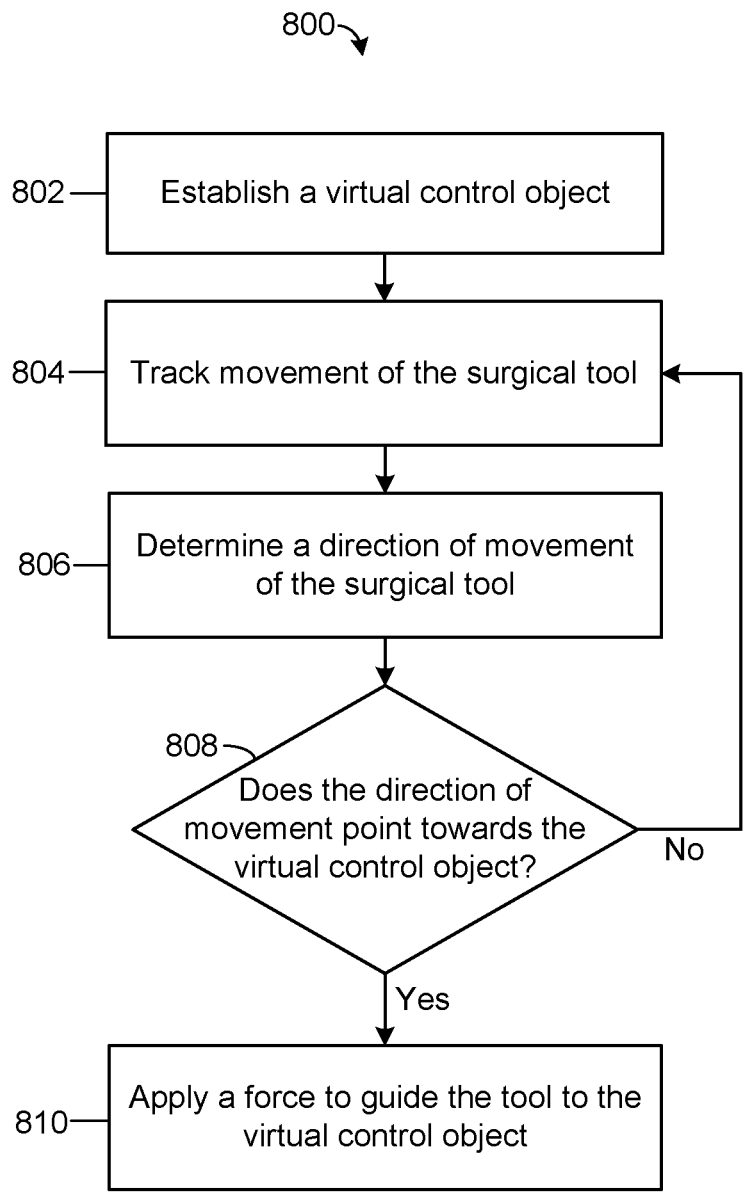
FIG. 8 is flowchart of a fourth process that can be executed by the surgical system of FIG. 2, according to an exemplary embodiment.

Referring now to FIG. 8, a flowchart illustrating a process 800 for guiding a surgical tool to a virtual control object (e.g., a haptic object) is shown, according to an exemplary embodiment. The process 800 can be executed by the surgical system 200, for example at step 308 of process 300.

At step 802, a virtual control object is established. That is, the virtual control object is generated and a pose of the virtual control object is defined. The virtual control object may include one or more of a point object, a line object, a planar object, or a three-dimensional surface or volume as described in detail above with reference to FIG. 2. In some cases, the virtual control object is a haptic object. Process 800 may be adapted for use with various virtual control objects having various shapes.

At step 804, movement of the surgical tool 234 is tracked (e.g., by the tracking system 222). For example, the position of a point associated with the surgical tool 234 (e.g., a tool center point) can be determined and updated over time. The position of the point may be defined relative to the virtual control object, i.e., in a coordinate system in which the pose of the virtual control object is also defined. The surgical tool 234 may be caused to move by manipulation by a user.

At step 806, a direction of movement of the surgical tool is determined (e.g., by the processing circuit 260). For example, the position of the point associated with the surgical tool 234 can be repeatedly collected over time to obtain a time series of position data. Given two positions (e.g., for subsequent time steps), a vector can be defined which characterizes the direction of movement of the surgical tool 234 (e.g., a velocity vector). In some cases, the speed of movement (e.g., a magnitude of the velocity vector) is determined based on the distance between the positions used and the elapsed time between collection of those data points. In some cases, the process 800 does not proceed to step 808 unless the magnitude of the velocity vector exceeds a threshold value.

At step 808, a determination is made (e.g., by the processing circuit 260) regarding whether the direction of movement points towards the virtual control object. For example, a velocity vector determined at step 806 may be extended (e.g., infinitely) from the latest tracked position of the surgical tool in the direction of movement. If the extended velocity vector intersects the virtual control object, for example, a determination may be made that the direction of movement points towards the virtual control object. If the extended velocity vector does not intersect the virtual control object, a determination may be made that the direction of movement does not point towards the virtual control object. Various other statistical methods, coordinate transformations, etc. may be used in various embodiments to determine whether the direction of movement of the surgical tool points toward the virtual control object. For example, in some embodiments a target volume is defined at (e.g., around, adjacent to, extending from) the virtual control object, and the direction of movement may be determined to be pointing towards the virtual control object if the extended velocity vector intersects the target volume. In a case where the virtual control object is a line, the target volume may be defined as a cylinder centered on the line, for example.

If the direction of movement does not point towards the virtual control object, the process 800 returns to step 804 where the movement of the surgical tool 234 is tracked. Steps 804-808 may be repeated until the direction of movement points towards the virtual control object.

If the direction of movement is determined as pointing towards the virtual control object, at step 810 the robotic device 220 is controlled to provide a force to guide the surgical tool 234 to the virtual control object. For example, a positive assistive force may be provided which assists a user in moving the surgical tool 234 toward the virtual control object. The positive assistive force may be insufficient to independently move the surgical tool 234 without an external force supplied by a user. In some cases, force applied at step 810 causes the surgical tool to automatically move (without user manipulation) to the virtual control object. As another example, in some embodiments the force is provided as a haptic boundary (e.g., a collapsing haptic boundary) that constrains the surgical tool 234 from moving away from the virtual control object and/or from deviation from a direction of movement towards the virtual control object.

The surgical system 200 may thereby execute process 800 to facilitate a user in moving the surgical tool to the virtual control object in response to the user initiation movement of the surgical tool towards the virtual control object. For example, various movements of the surgical tool away from the virtual control object may be desired to properly position the surgical tool 234, the robotic arm 232, anatomical structures, other surgical equipment, etc. before use of the virtual control object is desired. Process 800 provides a user-friendly, efficient workflow in which the surgical tool can be moved freely until the surgical tool is moved towards the virtual control object (e.g., towards a surgical field at which the virtual control object is located), at which point the system 200 automatically initiates guidance of the surgical tool to the virtual control object.

Referring now to FIGS. 9-10, a process for providing a haptic interaction including a damping zone is shown, according to an exemplary embodiment. FIG. 9 shows a process 900 for providing a haptic interaction including a damping zone, while FIG. 10 illustrates an example haptic object that includes a damping zone. The process 900 can be executed by the surgical system 200, for example at step 310 of process 300. Although a cylindrical haptic object is shown in FIG. 10 for the sake of example, it should be understood that that the features of FIGS. 9-10 can be adapted for use with virtual control objects of various geometries.

At step 902, a haptic object having a damping zone is established (e.g., defined in virtual space by the processing circuit 260). The damping zone may be defined as a sub portion of the haptic object and/or as a region within the haptic object. An example haptic object 1000 having a damping zone 1002 is shown in FIG. 10. As shown in FIG. 10, the haptic object 1000 is a cylindrical haptic object and the damping zone 1002 is a cylindrical disk positioned in the haptic object 1000. In the example of FIG. 10, the haptic object 1000 and the damping zone 1002 have an equal diameter while the height of the damping zone 1002 is significantly less than a height of the haptic object 1000, and are centered on a shared axis 1004. In other embodiments, various relative sizes and dimensions are possible.

In some examples, the damping zone 1002 is positioned along the haptic object 1000 proximate a surface of an anatomical feature (e.g., a bone). For example the damping zone 1002 may be on an exterior side of a surface of a bone. In such a case, as a tracked surgical tool 234 approaches the bone while constrained by the haptic object 1000, the surgical tool 234 first reaches the damping zone 1002.

At step 904, a determination is made (e.g., by the processing circuit 260 using data form the tracking system 222) that the surgical tool 234 has entered a first side of the damping zone 1002. In the example of FIG. 10, a position of a TCP of the surgical tool 234 may be tracked relative to the damping zone 1002, and the surgical tool 234 may be determined to have entered the first side of the damping zone 1002 when the TCP intersects the first surface 1006 of the damping zone 1002.

At step 906, the robotic device 220 is controlled to provide haptic feedback partially resisting movement of the surgical tool through the damping zone. For example, control of the robotic device 220 based on the damping zone may cause movement of the surgical tool 234 to be slowed (e.g., to not exceed a preset speed) as the surgical tool 234 passes through the damping zone. In cases where the damping zone is positioned at a surface of a bone, the damping zone may therefore act to manage (e.g., reduce) a speed of translation of the surgical tool 234 at initial impact between the surgical tool 234 and the bone. By reducing speed of translation of the surgical tool 234, the damping zone as provided by process 900 may thereby reduce skiving, increase the quality of a cut or bore/drill hole, and increase the accuracy of cut or hole placement.

Although FIGS. 9-10 show a damping zone in which movement of the robotic device 220 is damped as described above, in other embodiments other types of zones associated with other effects are provided, in which case step 906 is adapted accordingly. For example, in some embodiments the damping zone is replaced with an accelerating zone in which the robotic device 220 causes velocity of the surgical tool 234 to be increased as the surgical tool passes through the accelerating zone at step 906. As another example, in some embodiments, the damping zone is replaced with an attractive zone, in which the robotic device 220 in controlled to provide a force on the surgical tool 234 oriented toward a position in the attractive zone (e.g., a midpoint of the attractive zone), or a repulsive zone, in which the robotic device 220 is controlled to provide a force on the surgical tool 234 oriented away from a position in the repulsive zone.

At step 908, a determination is made (e.g., by the processing circuit 260 using data from the tracking system 222) that the surgical tool exited a second side of the damping zone. In the example of FIG. 10, a position of a TCP of the surgical tool 234 may be tracked relative to the damping zone 1002, and the surgical tool 234 may be determined to have exited the second side of the damping zone 1002 when the TCP passes the second side 1008 of the damping zone 1002.

At step 910, in response to the determination that the surgical tool has exited the second side of the damping zone, the damping zone is removed from the haptic object (e.g., by the processing circuit 260). The resistive feedback applied at step 906 is no longer applied. In some embodiments, the surgical tool can the repeatedly pass through the region previously occupied by the damping zone without experiencing the resistance of step 906. Accordingly, the surgical system 200 can be configured to provide a damping resistance to facilitate initial contact between the surgical tool 234 and a bone, and to automatically remove such resistance after the initial contact.

Figure 11:
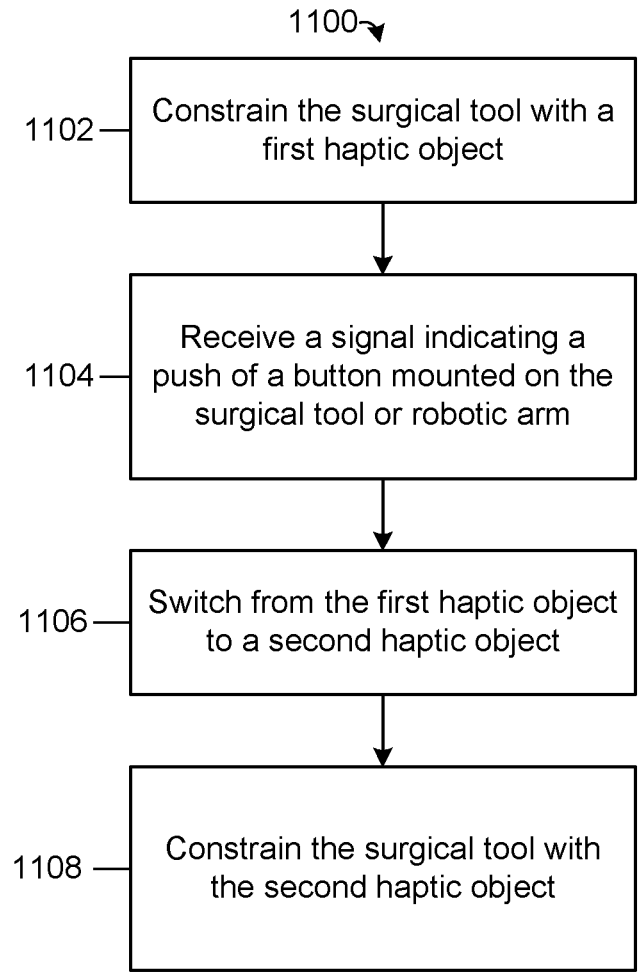
FIG. 11 is a flowchart of a sixth process that can be executed by the surgical system of FIG. 2, according to an exemplary embodiment.
Figure 12:
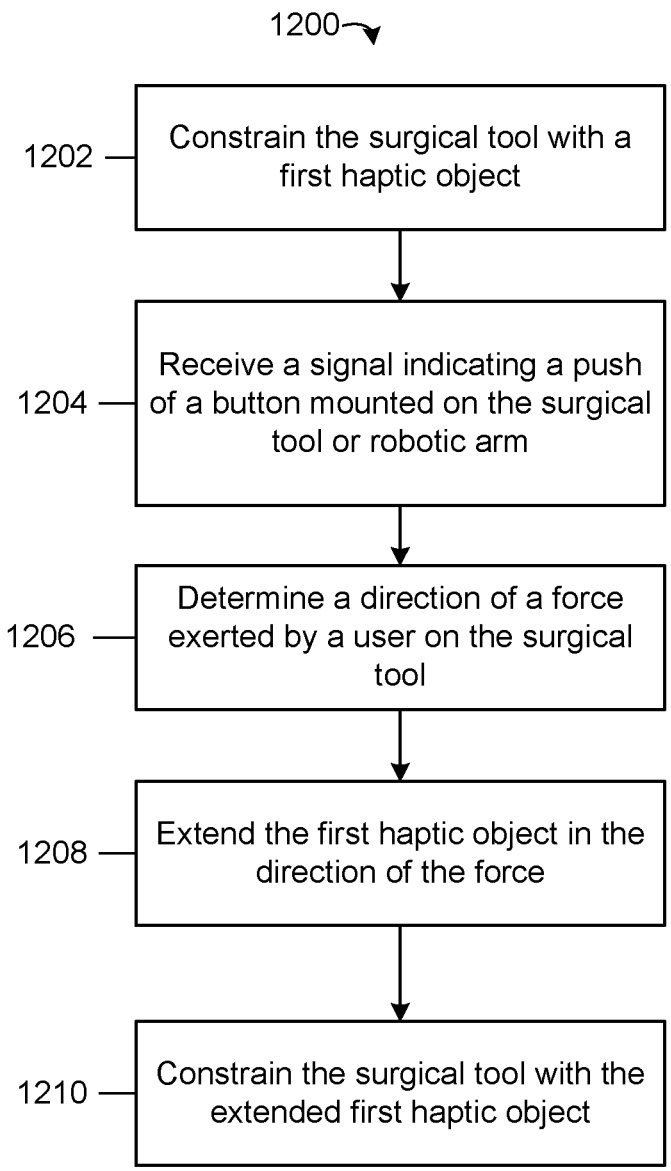
FIG. 12 is a flowchart of a seventh process that can be executed by the surgical system of FIG. 2, according to an exemplary embodiment.
Figure 13:
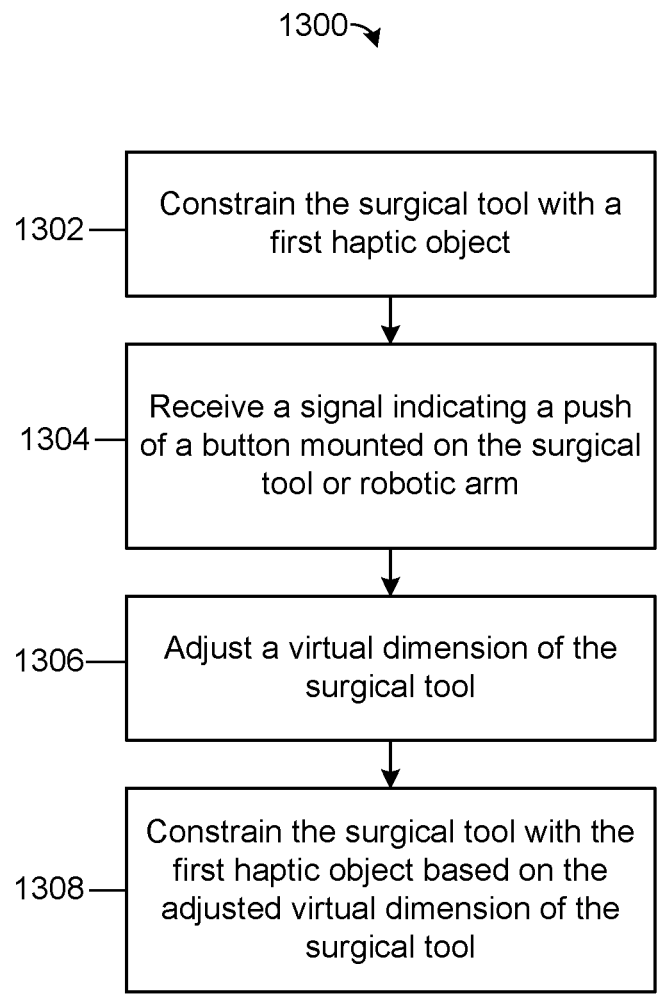
FIG. 13 is a flowchart of a eighth process that can be executed by the surgical system of FIG. 2, according to an exemplary embodiment.

Referring now to FIGS. 11-13, flowcharts showing processes for adjusting a haptic interaction in response to an input received from a user via a button (key, trigger, switch, pressure sensor, hand position sensor, etc.) mounted on the surgical tool or robotic arm are shown, according to exemplary embodiments. With reference to FIG. 2, the processes of FIGS. 11-13 contemplate a button positioned on a grip or handle region of the robotic arm 232 or surgical tool 234, such that the button is readily available to the user (e.g., a surgeon) while the user manipulates the robotic arm 232 and surgical tool 234 during execution of a surgical procedure. The button may be selected by the user without requiring the user to change the user's grip on the robotic arm 232 and/or the surgical tool 234 and without requiring the user to turn the user's vision or attention away from the surgical field. The processes of FIGS. 11-13 may be executed by the surgical system 200, for example as part of step 310 of FIG. 3.

FIG. 11 shows a flowchart of a process 1100 in which the button allows a user to switch between a first haptic object and a second haptic object. At step 1102, the surgical tool 234 is constrained with a first haptic object. The first haptic object may have any of the dimensions, shapes, etc. described herein. At step 1104, an electrical signal is received (e.g., at the processing circuit 260) indicating a push of the button mounted on the surgical tool or robotic arm. At step 1106, haptic control of the surgical tool 234 is switched form the first haptic object to the second haptic object, such that, at step 1108, the surgical tool 234 is constrained with the second haptic object. In some cases, the button can be pushed again to return to control based on the first haptic object.

The process 1100 may provide various advantages based on the relative sizes, shapes, etc. of the first haptic object and the second haptic object. In some embodiments, the first haptic object is a sub-portion of the second haptic object (i.e., such that the second haptic object allows a larger range of motion than the first haptic object). In such a case, a user may select a button to allow the surgical tool 234 to reach areas which the surgical tool was constrained from reaching under control based on the first haptic object. One example is a set of planar haptic objects, wherein the first haptic object corresponds to a virtually-determined extent of a planar cut, while the second haptic object is a larger, coplanar object. Based on the surgeon's experience and intraoperative observations, the surgeon can push the button to extend the cut intraoperatively if needed. As another example, the first haptic object and the second haptic object may only be partially overlapping. In such an example, the process 1100 may facilitate switching between different steps of a surgical procedure. In some embodiments, the processing circuit 260 prevents switching between the haptic control objects unless the surgical tool is currently located within both haptic objects.

FIG. 12 shows a process 1200 in which the button allows a user to cause the haptic object to be extended in a direction of force exerted by the user. At step 1202, the surgical tool is constrained with a first haptic object. The first haptic object may have any of the dimensions, shapes, etc. described herein. At step 1204, an electrical signal is received (e.g., at the processing circuit 260) indicating a push of the button mounted on the surgical tool or robotic arm.

At step 1206, in response to the signal from the button, a direction of a force exerted on the surgical tool is determined (e.g., by the processing circuit 260). A HIP of the surgical tool may be positioned at a boundary of the first haptic object, such that the haptic control interaction prevents the force from causing the surgical to move further in the direction of the force. In such a scenario, the push of the button indicates that the user desires to move the surgical tool further in the direction of the force. Accordingly, at step 1208, the first haptic object is extended in the direction of the force, thereby allowing the surgical tool to be moved further in said direction before being constrained by the first haptic object. The first haptic object maybe extended by a preset distance or volume at step 1208. The surgical tool is then constrained by the extended first haptic object.

Process 1200 may thereby facilitate a user in extending a surgical tool beyond the first haptic object in a particular, user-selected direction. For example, in some cases, control based on the first haptic object may constrain the surgical tool from reaching a full extent of an anatomical feature which a surgeon desires to modify with the surgical tool. The surgeon may then force the surgical tool towards the target feature and select the button to cause the haptic object to be extended towards the target feature. Process 1200 thereby facilitates advantageous intraoperative adjustments to the haptic object.

FIG. 13 shows a process 1300 in which the button allows a user to adjust a virtual dimension of the virtual tool, thereby adjusting a virtual control interaction. In the embodiments contemplated by process 1300, a haptic control interaction is achieved by tracking a haptic interaction point (e.g., a TCP) associated with the surgical tool. The HIP is a one-dimensional point. The processing circuit uses one or more virtual dimensions of the surgical tool to determine the volume occupied by the surgical tool based on the position of the HIP. For example, for a spherical burr, the HIP may be located at a center of the spherical burr and a radius of the burr may be used to determine, in virtual space, the 3-D volume occupied by the spherical burr based on the HIP position and the radius dimension. Haptic control is provided based on an interaction between the volume occupied by the surgical tool (or a boundary thereof) and a haptic object. In the spherical burr example, the HIP may be constrained to positions offset from a haptic boundary by at least the radius dimension of the spherical burr. In such a case, changing the virtual radius of the spherical burr can allow the HIP to be moved closer to the haptic boundary. Therefore, control of the robotic device can be altered by modifying a virtual dimension of the surgical tool.

At step 1302, the surgical tool is constrained with a first haptic object. The first haptic object may have any of the dimensions, shapes, etc. described herein. At step 1304, an electrical signal is received (e.g., at the processing circuit 260) indicating a push of the button mounted on the surgical tool or robotic arm. At step 1306, a virtual dimension of the surgical tool is adjusted (e.g., by the processing circuit 260) in response to the signal from the button. For example, in a scenario where the surgical tool is a spherical burr, the virtual radius of the spherical burr may be reduced.

At step 1308, the robotic device is controlled to constrain the surgical tool with the first haptic object based on the adjusted virtual dimension of the surgical tool. In an example where the virtual dimension of surgical tool is reduced (e.g., where a radius is decreased), the surgical tool may be provided with a larger range of motion at step 1308 as compared to step 1302. In such a case, a surgeon may engage the button when the surgeon desires that the surgical tool be allowed to reach a position which the surgical tool is constrained from reaching at step 1302. The position of the virtual center point of the surgical tool may also be shifted relative to the tracked position of the surgical tool (e.g., at step 1306), for example such that the reduced-size virtual tool aligns with a border of the original-sized virtual tool. This shift may provide the surgical tool with a larger range of motion in some directions while preserving the range of motion along the shared border. For example, shifting the virtual center point towards a distal tip of the surgical tool when reducing the virtual dimension of the surgical tool may allow for increased side-to-side range of motion (i.e., orthogonal to the axis of the surgical tool) while confining the surgical tool to the original cut depth. Process 1300 may thereby facilitate minor intraoperative adjustments to the extent of an anatomical features which can be modified by the surgical tool in accordance with the surgical plan.

In some embodiments, the button can be repeatedly selected to cause repeated adjustments to one or more virtual dimensions of the surgical tool (e.g., stepping to increasingly smaller sizes, switching between two available sizes, sequentially moving through three or more available sizes, etc.). Many such possibilities are within the scope of the present disclosure.

In other embodiments, the input is received from another source (e.g., a foot pedal, voice activation, mouse, keyboard, touch screen, etc.). In other embodiments, the user input (described in FIGS. 11-13 as originating at a button) is replaced by an automatic response based on a tracked position or behavior of the surgical tool and/or robotic device. For example, in some embodiments, a dwell time of the surgical tool at a boundary of the haptic object is detected. When the dwell time exceeds a threshold amount of time, haptic control may be modified as described at step 1106-1108, 1206-1210, and/or 1306-1308. Various such modifications are within the scope of the present disclosure.

As mentioned above, all combinations of the various features illustrated in FIGS. 4-13 are within the scope of the present disclosure. For example, the process 300 can be implemented using the steps of one or more of process 400, process 600, process 800, process 900, process 1100, process 1200, and process 1300. Furthermore, it should be understood that the various features, method steps, etc. described herein may be adapted for use in facilitating a variety of surgical procedures, including total and partial hip, knee, and shoulder arthroplasty procedures, as well as for use in executing non-surgical tasks.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. The systems described herein may be adapted to execute the methods described herein. Other substitutions, modifications, changes, and omissions may be made in the design, operating conditions and arrangement of the exemplary embodiments without departing from the scope of the present disclosure.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and are considered to be within the scope of the disclosure.

What is claimed is:

1. A method, comprising:
defining a virtual object;
defining a first point and a second point associated with a virtual representation of a surgical tool, wherein movement of the virtual representation of the surgical tool corresponds to movement of the surgical tool in real space;
constraining, by a robotic device coupled to the surgical tool, the first point to the virtual object while allowing, by the robotic device, unconstrained rotation of the second point about the first point before the first point reaches a threshold position along the virtual object;

automatically rotating, by the robotic device and in response to the first point reaching the threshold position along the virtual object, the surgical tool to align the second point to the virtual object;

constraining, in response to the second point reaching the virtual object, the first point and the second point to the virtual object;

determining whether a direction of a force exerted on the tool is within a threshold angle of a pre-determined exit direction;

in response to a determination that the direction of the force exerted on the tool is within the threshold angle of the pre-determined exit direction, determining whether the force exerted on the tool exceeds a threshold force; and in response to a determination that the force exerted on the tool exceeds the threshold force, controlling the robotic device to allow the first point and the second point to deviate from the virtual object.

2. The method of claim 1, wherein controlling the robotic device to constrain the first point to the virtual object comprises controlling the robotic device to prevent movement of the first point away from the virtual object, wherein the first point is associated with a cutting tip of the surgical tool.

3. The method of claim 1, further comprising:
defining a damping zone along the virtual object; and
in response to the first point entering the damping zone, controlling the robotic device to reduce a velocity of the first point while allowing movement of the first point through the damping zone.

4. The method of claim 3, comprising:
determining that the first point has passed through the damping zone; and
in response to a determination that the first point has passed through the damping zone, removing the damping zone from the virtual object while continuing to control the robotic device to constrain the first point to the virtual object.

5. The method of claim 1, wherein allowing, by the robotic device, the unconstrained rotation of the second point comprises allowing unconstrained rotation of a shaft of the surgical tool around a cutting tip of the surgical tool.

6. The method of claim 1, comprising:
determining that the first point is moving toward the virtual object; and
in response to a determination that the first point is moving towards the virtual object, controlling the robotic device to provide an assistive force to the surgical tool, the assistive force oriented to facilitate movement of the first point to the virtual object, wherein the assistive force is insufficient to independently move the surgical tool and combines with an external force supplied by a user to move the first point toward the virtual object.

7. The method of claim 1, comprising:
receiving a signal and a user defined direction; and
adjusting a haptic control interaction between the first point and the virtual object in response to the signal by extending the virtual object in the user-defined direction.

8. The method of claim 1, wherein defining the virtual object comprises:
obtaining a surgical plan comprising a planned hole in a target bone; and
aligning the virtual object with the planned hole.

9. The method of claim 1, wherein the threshold position along the virtual object corresponds to a threshold distance from an anatomical feature.

10. The method of claim 1, wherein the threshold position along the virtual object corresponds to an amount of penetration into an anatomical feature.

11. The method of claim 1, wherein the virtual object is a virtual line.

12. A method, comprising:
defining a virtual object;
defining at least one point associated with a virtual representation of a surgical tool, wherein movement of the virtual representation of the surgical tool corresponds to movement of the surgical tool in real space;
constraining, by a robotic device interfacing with the surgical tool, the at least one point to the virtual object;
determining whether a direction of a force exerted on the tool is within a threshold angle of a pre-determined exit direction;
in response to a determination that the direction of the force exerted on the tool is within the threshold angle of the pre-determined exit direction, determining whether the force exerted on the tool exceeds a threshold force; and
in response to a determination that the force exerted on the tool exceeds the threshold force, controlling the robotic device to allow the at least one point to deviate from the virtual object.

13. A system, comprising:
a surgical tool;
a robotic device coupled to the surgical tool; and
a control system programmed to:
define a first point and a second point associated with a virtual representation of a surgical tool, wherein movement of the virtual representation of the surgical tool corresponds to movement of the surgical tool in real space;
control the robotic device coupled to the surgical tool to constrain the first point to a virtual object while allowing unconstrained rotation of the second point about the first point before the first point reaches a threshold position along the virtual object; and
in response to the first point reaching the threshold position along the virtual object, control the robotic device to automatically rotate the surgical tool to align the second point to the virtual object
constrain, in response to the second point reaching the virtual object, the first point and the second point to the virtual object;
determine whether a direction of a force exerted on the tool is within a threshold angle of a pre-determined exit direction;
in response to a determination that the direction of the force exerted on the tool is within the threshold angle of the pre-determined exit direction, determine whether the force exerted on the tool exceeds a threshold force; and
in response to a determination that the force exerted on the tool exceeds the threshold force, control the robotic device to allow the first point and the second point to deviate from the virtual object.

14. The system of claim 13, wherein the control system is programmed to control the robotic device to constrain the first point to the virtual object by controlling the robotic device to prevent movement of the first point away from the virtual object, wherein the first point is associated with a cutting tip of the surgical tool.

15. The system of claim 13, wherein the control system is further programmed to constrain, in response to the second point reaching the virtual object, the first point and the second point to the virtual object by controlling the robotic device to prevent movement of the first point and the second point away from the virtual object, wherein the first point is associated with a cutting tip of the surgical tool and the second point is associated with a shaft of the surgical tool.

16. The system of claim 15, wherein the surgical tool is a cutting tool.

17. The system of claim 13, wherein the control system is further configured to:
define a damping zone along the virtual object;
determine that the first point is in the damping zone;
control the robotic device to resist movement of the first point through the damping zone from a first position along the virtual object to a second position along the virtual object;
determine that the first point has passed through the damping zone; and
in response to a determination that the first point has passed through the damping zone, remove the damping zone from the virtual object while continuing to control the robotic device to constrain the first point to the virtual object.

18. The system of claim 13, wherein the control system is further programmed to determine that the first point is moving toward the virtual object and, in response to a determination that the first point is moving towards the virtual object, control the robotic device to provide an assistive force to the surgical tool, the assistive force oriented to facilitate movement of the first point to the virtual object.

19. The system of claim 13, wherein the control system is further programmed to receive a signal and a user defined direction and adjust a haptic control interaction between the first point and the virtual object in response to the signal by extending the virtual object in the user-defined direction.

* * * * *